(12) United States Patent
Jinks et al.

(10) Patent No.: US 9,067,031 B2
(45) Date of Patent: Jun. 30, 2015

(54) METERED DOSE VALVES AND DISPENSERS

(75) Inventors: Philip A. Jinks, Loughborough (GB);
Graham R. Purkins, Loughborough (GB); Peter D. Hodson, Breaston (GB);
Paul E. Hansen, Lake Elmo, MN (US)

(73) Assignee: 3M INNOVATIVE PROPERTIES COMPANY, Saint Paul, MN (US)

( * ) Notice: Subject to any disclaimer, the term of this patent is extended or adjusted under 35 U.S.C. 154(b) by 1524 days.

(21) Appl. No.: 12/444,864

(22) PCT Filed: Oct. 19, 2007

(86) PCT No.: PCT/US2007/081933
§ 371 (c)(1),
(2), (4) Date: May 3, 2010

(87) PCT Pub. No.: WO2008/049107
PCT Pub. Date: Apr. 24, 2008

(65) Prior Publication Data
US 2010/0199983 A1 Aug. 12, 2010

(30) Foreign Application Priority Data
Oct. 19, 2006 (GB) .................................. 0620700.5

(51) Int. Cl.
*A61M 11/00* (2006.01)
*A61M 15/00* (2006.01)
(Continued)

(52) U.S. Cl.
CPC ......... *A61M 15/009* (2013.01); *A61M 2205/75* (2013.01); *B65D 83/54* (2013.01); *B65D 83/754* (2013.01)

(58) Field of Classification Search
USPC .............. 128/200.23, 200.14, 200.11, 15–23; 222/402.2, 189.06, 8, 9, 11
See application file for complete search history.

(56) References Cited

U.S. PATENT DOCUMENTS 2,741,319 A * 4/1956 Mickelsen .................... 169/87
2,815,889 A 12/1957 Stetz et al.
3,968,905 A 7/1976 Pelton
(Continued)

FOREIGN PATENT DOCUMENTS

EP 0 372 777 6/1990
GB 837465 6/1960
(Continued)

OTHER PUBLICATIONS

Ullmann's Encyclopedia of Industrial Chemistry, 2000 Electronic Release under the article posted Jun. 15, 2000 entitled "Metallic Foams" by Weber, Banhart and Baumeister.
(Continued)

*Primary Examiner* — Tan-Uyen (Jackie) T Ho
*Assistant Examiner* — Mark Wardas
(74) *Attorney, Agent, or Firm* — 3M Innovative Properties Company

(57) ABSTRACT

A metered dose valve for use in a pressurized metered dose dispenser for dispensing a metered dose of an aerosol formulation comprising particles of a medicament suspended in liquefied propellant, optionally in combination with one or more excipients, the valve comprising a metering chamber and at least one porous, fluid permeable, particulate semi-permeable body, the at least one porous body being positioned within a region of the interior conduit of the valve, for example within the metering chamber, or a pre-metering chamber and/or an internal channel upstream of the metering chamber.

17 Claims, 19 Drawing Sheets

(51) Int. Cl.
　　　*B65D 83/54*　　　(2006.01)
　　　*B65D 83/14*　　　(2006.01)

(56) References Cited

U.S. PATENT DOCUMENTS

| | | | |
|---|---|---|---|
| 4,142,652 A * | 3/1979 | Platt | 222/402.2 |
| 5,536,444 A | 7/1996 | Hettche et al. | |
| 5,772,085 A | 6/1998 | Bryant et al. | |
| 6,136,294 A | 10/2000 | Adjei et al. | |
| 6,315,173 B1 | 11/2001 | De Giovanni et al. | |
| 6,640,805 B2 | 11/2003 | Castro et al. | |
| 6,755,189 B2 * | 6/2004 | Ivri et al. | 128/200.16 |
| 7,185,648 B1 | 3/2007 | Rand | |

FOREIGN PATENT DOCUMENTS

| | | |
|---|---|---|
| GB | 994734 | 6/1965 |
| GB | 1 502 008 | 2/1978 |
| GB | 2 263 064 | 7/1993 |
| JP | 2001114360 | 4/2001 |
| WO | WO 91/11173 | 8/1991 |
| WO | WO 94/21228 | 9/1994 |
| WO | WO 94/21229 | 9/1994 |
| WO | WO 95/15151 | 6/1995 |
| WO | WO 98/58117 | 12/1998 |
| WO | WO 01/64273 | 9/2001 |
| WO | WO 01/64274 | 9/2001 |
| WO | WO 01/64275 | 9/2001 |
| WO | WO 01/64524 | 9/2001 |
| WO | WO 03/059317 | 7/2003 |
| WO | WO 03/059331 | 7/2003 |
| WO | WO 2007/112312 | 10/2007 |

OTHER PUBLICATIONS

Kona, No. 20 (2002) entitled "Synthesis and Fabrication of Inorganic Porous Materials: From nanometer to Millimeter Size" by Takahashi and Fuji under the sub-section "Synthesis of Spatial Pore".
Drug Delivery to the Respiratory Tract' ed. D. Ganderton and T. Jones, publ. Ellis Horwood, Chichester (1987), pp. 89-90.
Luis A. Dellamary et al., "Hollow porous particles in metered does inhalers," Pharmaceutical Research, 2000, vol. 17(2), pp. 168-174.
Extended European Search Report dated Mar. 6, 2014.

* cited by examiner

METERED DOSE VALVES AND DISPENSERS

CROSS REFERENCE TO RELATED APPLICATIONS

This application is a national stage filing under 35 U.S.C. 371 of PCT/US2007/081933, filed Oct. 19, 2007, which claims priority to Great Britain Application No. 0620700.5, filed Oct. 19, 2006, the disclosure of which is incorporated by reference in its/their entirety herein.

FIELD

This invention relates to metered dose valves and pressurized metered dose dispensers, in particular metered dose valves for metered dose inhalers and such inhalers. The valves and/or dispensers are advantageous for dispensing medicament, in particular aerosol formulations comprising medicament particles suspended in liquid propellant, for administration to the respiratory tract, for example for delivery by pulmonary or nasal inhalation.

BACKGROUND

Asthma and other respiratory diseases have long been treated by the inhalation of appropriate medicament. For many years a widely used and convenient choice of treatment has been the inhalation of medicament from an aerosol created by a pressurized metered dose inhaler (pMDI). Formulations used in pMDIs often comprise particles of medicament suspended in liquefied propellant(s), e.g. CFC propellant(s) and more recently non-CFC propellant(s), such as 1,1,1,2-tetrafluoroethane (HFA134a) and/or 1,1,1,2,3,3,3-heptafluoropropane (HFA227).

The consistency/uniformity of the metered dose delivered from a suspension-based pMDI may be compromised in a number of ways. In particular there is generally a difference between the specific gravity of the solid medicament to be dispensed and the liquid component of the aerosol formulation (for example propellant or propellant mixture or mixture of propellant(s) and, if used, liquid excipient(s)). This means that with time, the two components (solid and liquid) tend to separate with the more dense component(s) settling downwardly (sedimenting) and the less dense component(s) rising upwardly (creaming). In a number of medicinal aerosols, the medicament has a higher specific gravity (density) than that of the liquid component of the formulation (e.g. propellant(s)). This often holds true for formulations based on HFA134a. In such formulations the particles of medicament tend to sediment. In other formulations, where the medicament has a lower specific gravity than that of the liquid component of the formulation, the medicament particles tend to cream. The tendency of particles of a particular medicament to sediment or cream, as the case may be, may be accentuated by flocculation of the suspended medicament particles, whereby the flocculation of a suspension can increase the effective particle size from 10 microns or less to well over 1 mm due to the formation of large flocs. This holds particularly true when using HFA 134a and/or HFA 227, because suspensions of many drugs in formulations containing these propellants generally flocculate more coarsely and/or more rapidly than in formulations with CFC propellants.

In the majority of commercial pMDI devices, the metered dose to be administered is filled into the metering chamber of its metered dose valve just after releasing the device after actuation of the previous dose. Since a patient may use the pMDI device once or twice a day or only when needed, the next metered dose to be administered may be retained in the metering chamber for 12 hours, 24 hours or longer. Depending on the particular sedimentation or creaming behavior of the medicinal suspension formulation and/or the orientation of the pMDI device during such periods of non-use, it has been observed that there is a general tendency towards an undesired decrease in the concentration of suspended medicament within the metered dose retained in the metering chamber. Moreover, a tendency towards a loss of dose is generally observed due to sedimentation or creaming (as the case may be) of medicament out of the metering chamber generally back to the formulation chamber, despite the fact such pMDI devices typically include a tortuous flow path and/or a pre-metering chamber between the formulation chamber of the device and the metering chamber of the valve. Even if the amount of medicament loss for a metered dose retained in the metering chamber is relatively small, each such loss over the lifetime of pMDI device may collectively lead to an undesirable, ever-increasing rise in the overall concentration of medicament suspended in the formulation.

Some pMDI devices do not include such dose-retaining, metered dose valves, but rather include herein-called "empty-fill" metered dose valves. Here the valve is designed such that there is very open access to the metering chamber (for example large through-openings to the interior of the valve (e.g. to the pre-metering chamber or to the metering chamber)), so that the metering chamber can be "easily emptied" of formulation and "easily filled" with a fresh metered dose of suspension formulation. Examples of such empty-fill type metered dose valves include commercial valves marketed under the trade designations EasiFill BK361 (from Bespak, Bergen Way, King's Lynn, Norfolk, PE30 2JJ, UK) and DF30 ACT (from Valois SAS, Pharmaceutical Division, Route des Falaises, 27100 le Vaudreuil, France). Other metered dose valves for pMDIs, such as those disclosed and described in U.S. Pat. No. 5,772,085, operate under a shuttle principle, wherein the metering chamber is brought into the formulation chamber so that aerosol formulation can enter the metering chamber and subsequently moved out of the formulation chamber, sealed off and brought into communication with an outlet allowing the metered dose to pass to the patient. Such valves typically do not suffer loss of dose as described above in conjunction with dose-retaining-type valves, since the metering chamber is typically filled with the metered dose to-be-administered just prior to release (assuming that the user has properly used the pMDI device). Nonetheless dose consistency can still be an issue, in particular with suspension formulations having tendencies towards rapid sedimentation or creaming. Moreover although users of suspension aerosols are always instructed to shake (or agitate) a pMDI device immediately prior to use, even a short delay between shaking and actuation of the device may be sufficient to allow some sedimentation or creaming (as the case may be) to occur into or out of the metering chamber due to the open design of such valves, resulting in an undesired change in dose and hence the device dispensing and the user receiving, a dose containing an elevated or a reduced amount of the medicament, respectively.

SUMMARY OF THE INVENTION

There is an ongoing need to provide metering dose valves for pressurized metered dose dispensers, in particular for metered dose inhalers, which facilitate the prevention or reduction of a tendency towards loss of dose from or change in dose in the metering chamber and hence facilitate enhanced consistency in dispensing metered doses of suspension medicament aerosol formulations.

Surprisingly it has been found that by providing a metered dose valve with a porous, fluid permeable, particulate semi-permeable body within a region of the interior conduit of the valve, such as within an internal chamber and/or an internal channel within the valve, a valve is provided which allows for desirable dose consistency whereby a tendency towards loss of dose from or change in dose in the metering chamber is prevented or reduced.

Thus according to one aspect of the present invention there is provided a metered dose valve for use in a pressurized metered dose dispenser for dispensing a metered dose of an aerosol formulation comprising particles of a medicament suspended in liquefied propellant, optionally in combination with one or more excipients, said valve comprising a metering chamber and a porous, fluid permeable, particulate semi-permeable body, said porous body being positioned within a region of the interior conduit of the valve.

Depending on the particular design of the metered dose valve and/or the properties of the particular porous body (e.g. selected material, structural integrity of material), a single porous body may be provided or alternatively, as desired and/or needed, two or more porous bodies may be provided. Accordingly herein the wording "a porous body" is preferably understood to mean "at least one porous body" and the wording "the porous body" to mean "the at least one porous body".

Depending on the particular design and/or type of metered dose valve, the porous body may be desirably positioned within an internal chamber or an internal channel (if present) upstream of the metering chamber or within both the chamber and channel. More particularly the porous body may be desirably positioned within the metering chamber, within a pre-metering chamber (if present), and/or within an internal channel or channels (if present) upstream of the metering chamber, such as an internal channel leading into the metering chamber and/or an internal channel between the pre-metering chamber and metering chamber.

Without wishing to become bound to any particular theory, it seems the porous body acts to hold medicament particles substantially uniformly dispersed within its volume limiting or preventing any extensive flocculation and/or sedimentation or creaming, as the case may be, and/or the porous body acts substantially as an appropriate barrier to large particulates (e.g. large flocs) and/or sediment or cream, as the case may be. For example in preferred embodiments in which the porous body is positioned within the metering chamber of the valve, the porous body, acting to hold medicament particles substantially uniformly dispersed within its volume, limits or prevents sedimentation or creaming, as the case may be, of medicament particles out of the metering chamber (e.g. for dose-retaining type metered dose valves) and/or acting as a type of barrier, prevents sedimentation or creaming, as the case may be, into or out of the metering chamber (e.g. for empty-fill-type metered dose valves). Alternatively in other preferred embodiments in which the porous body is positioned within internal channel(s) leading to the metering chamber and/or within a pre-metering chamber, the porous body acts substantially as a barrier limiting or preventing sedimentation or creaming, as the case may be, into or out of the metering chamber.

Another aspect of the present invention is the provision of a pressurized metered dose dispenser for dispensing an aerosol formulation comprising particles of a medicament suspended in liquefied propellant, optionally in combination with one or more excipients, the dispenser comprising an aerosol container equipped with a metered dose valve in accordance with the invention as described herein.

Metered dose valves and dispensers described herein are particularly suitable for use with dispensing suspension medicament aerosol formulations comprising HFA 134a and/or HFA 227 as propellant. Metered dose valves and dispensers, described herein are also particularly suitable for use in or as metered dose inhalers.

Further embodiments in accordance with the present invention are described in dependent claims.

BRIEF DESCRIPTION OF DRAWINGS

The invention will now be described with reference to the accompanying drawings in which:

FIG. 6 represents a schematic cross-sectional view of an exemplary embodiment of a metered dose valve in accordance with the invention, while

(It is to be recognized that for the schematic cross-sectional views of embodiments, in some cases for ease in viewing shading/cross-hatching e.g. in the background may have been omitted.)

DETAILED DESCRIPTION

It is to be understood that the present invention covers all combinations of particular, suitable, desirable, favorable, advantageous and preferred aspects of the invention described herein.

Figure 1A:
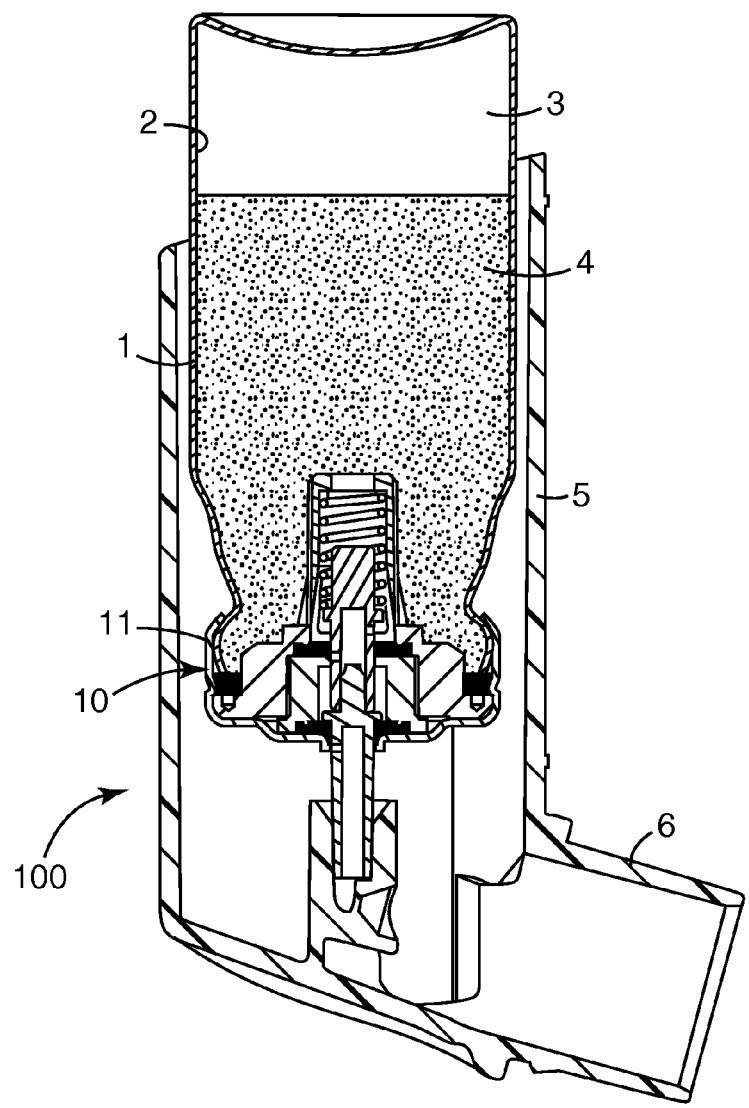
FIG. 1a represents a schematic cross-sectional view of a pressurized metered dose inhaler known in the art and FIG. 1b represents an enlarged view of a portion (i.e. the metered dose valve) of the inhaler.

For better understanding of the present invention, in the following an exemplary, known pressurized metered dose inhaler (FIG. 1) as well as other known metered dose valve for pressurized metered dose inhalers (FIGS. 2 to 5) will be first described. In particular, FIG. 1a shows a metered dose dispenser (100), in particular an inhaler, including an aerosol container (1) fitted with a metered dose valve (10) (shown in its resting position). The valve is typically affixed onto the container via a cap or ferrule (11) which is generally provided as part of the valve assembly. The illustrated valve is a commercial valve marketed under the trade designation BK357 of Bespak, Bergen Way, King's Lynn, Norfolk, PE30 2JJ, UK. As shown in FIG. 1a, the container/valve dispenser is typically provided with an actuator (5) including an appropriate patient port (6), such as a mouthpiece. For administration to the nasal cavities the patient port is generally provided in an appropriate form (e.g. smaller diameter tube, often sloping upwardly) for delivery through the nose. The inner walls (2) of the container and the outer walls of the portion(s) of the metered dose valve located within the container define a formulation chamber (3) in which aerosol formulation (4) is contained. Depending on the particular metered dose valve and/or filling system, aerosol formulation may be filled into the container either by cold-filling (in which chilled formulation is filled into the container and subsequently the metered dose valve is fitted onto the container) or by pressure filling (in which the metered dose valve is fitted onto the container and then formulation is pressure filled through the valve into the container). The valve shown in FIG. 1 a, better viewed in FIG. 1 b, includes a metering chamber (12), defined in part by an inner valve body housing (13), through which a valve stem (14), made of two components (14a, 14b), passes. The valve stem, which is biased outwardly by a compression spring (15), is in sliding sealing engagement with an inner tank seal (16) and an outer diaphragm seal (17). The valve also includes a valve body housing (20) in the form of a spring cage with two slots (21) and an opening at the top (21') allowing communication between the formulation chamber (3) and a pre-metering chamber (22). In the interior of the valve, aerosol formulation (4) can pass from the pre-metering chamber (22) into the metering chamber (12) via an internal flow channel (34) within the valve stem (14). (From ease in viewing, the cross-hatching representing aerosol formulation has not been included within the region of the interior conduit of the valve, e.g. the pre-metering chamber (22), the flow channel (34) and metering chamber (12) in the Figure.) To actuate (fire) the valve, the valve stem (14) is pushed inwardly relative to the container from its resting position shown in FIGS. 1 a and b, allowing formulation to pass from the metering chamber through a side hole (19) in the valve stem and through a stem outlet (24) to an actuator nozzle (7) then out to the patient. When the valve stem (14) is released, formulation enters into the interior of the valve, in particular into the pre-metering chamber (22), through the slots and opening (21 and 21') and thence from the pre-metering chamber through side holes (33a, 33b) and the flow channel (34) in the valve stem into the metering chamber (12).

As mentioned above, FIGS. 2 to 5 show other known metered dose valves used in pMDIs. Similar to the valve shown in FIG. 1, the valves of FIGS. 2 to 5 are typically fitted via a ferrule (11) onto an aerosol container. For the sake of ease in understanding and comparison, similar components of the respective valves are identified with like reference numbers in the Figures.

Figure 1B:
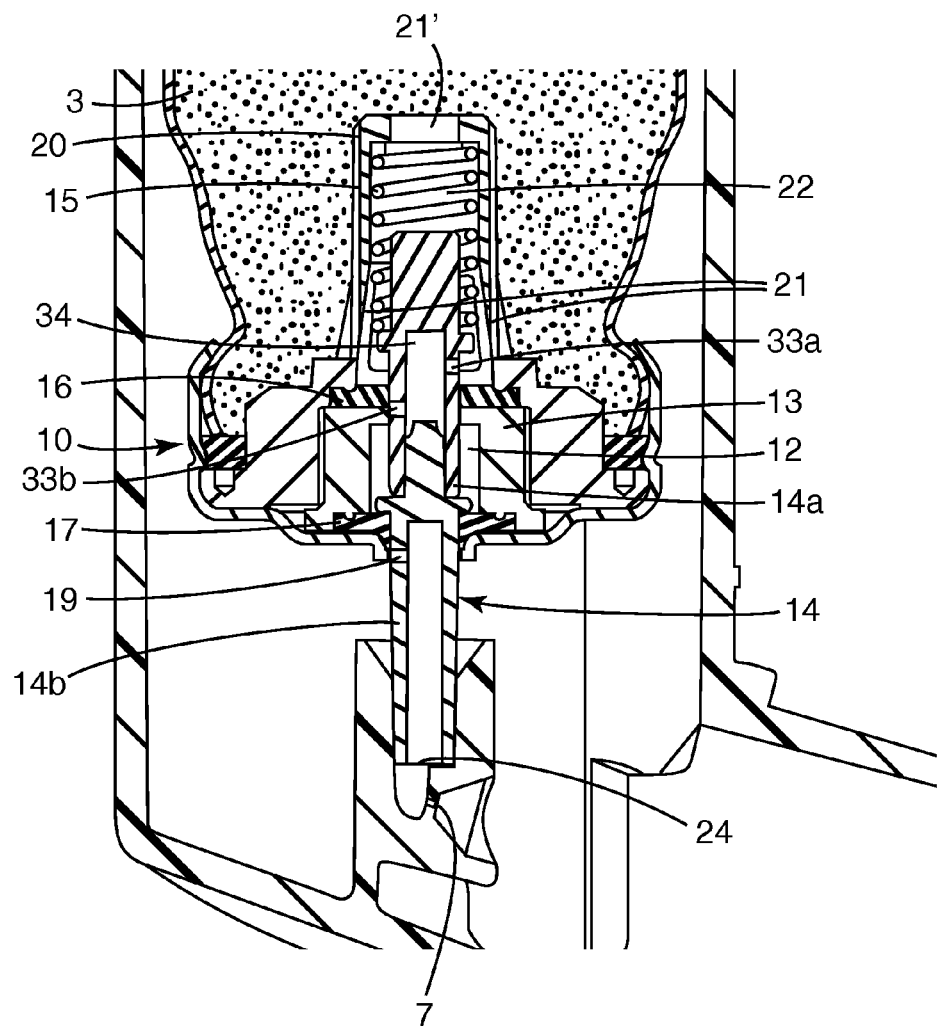
Figure 2:
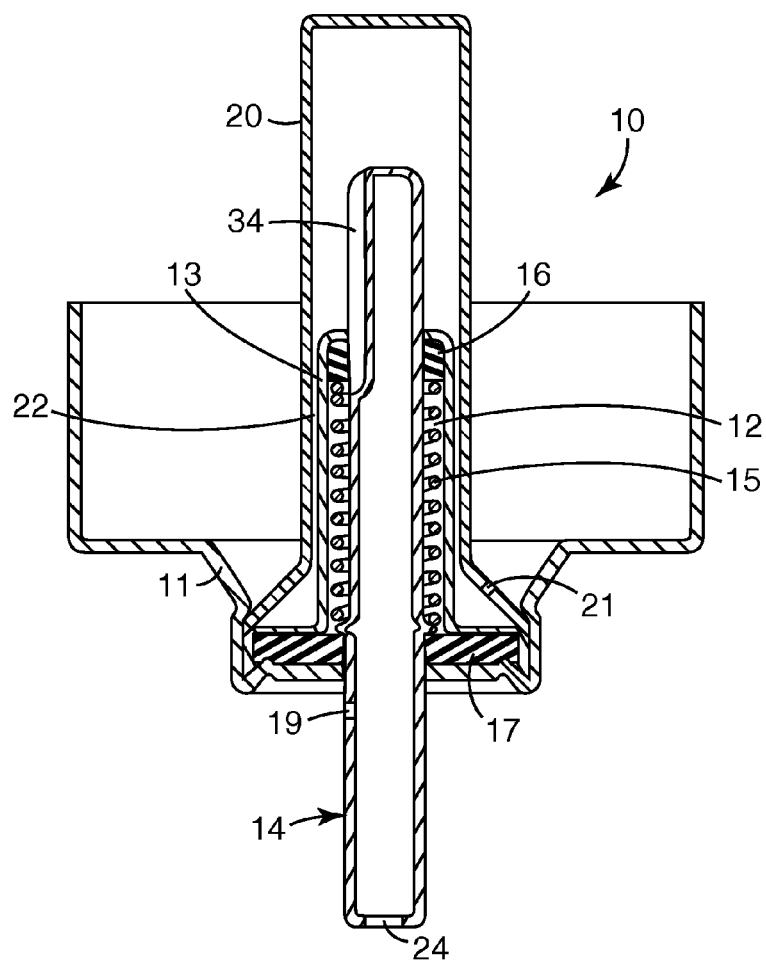
FIGS. 2 to 5 represent schematic cross-sectional views of further metered dose valves known in the art for use in pressurized metered dose inhalers.

FIG. 2 shows a commercial metered dose valve (10), in its resting position, supplied by 3M Drug Delivery Systems, 3M Health Care Limited, Morely Street, Loughborough, UK. Similar to the valve shown in FIG. 1, the valve includes a metering chamber (12), defined in part by an inner valve body housing (13), through which a valve stem (14) passes. The valve stem, which is biased outwardly by a compression spring (15) located within the metering chamber (12), is in sliding sealing engagement with an inner tank seal (16) and an outer diaphragm seal (17). The valve also includes a valve body housing (20), in this case, in the form of a tank retaining cup. The operation of the valve is similar to that described above for the valve shown in FIG. 1, whereby the valve stem (14) is pushed inwardly relative to the container allowing formulation to pass from the metering chamber through a side hole (19) in the valve stem and through a stem outlet (24) to an actuator nozzle (not shown) then out to the patient and when the valve stem (14) is released, formulation enters into the valve, in particular through an opening (21) into a pre-metering chamber (22), and thence from the pre-metering chamber through a groove (34) in the valve stem past the inner tank seal (16) into the metering chamber (12).

Figure 3:
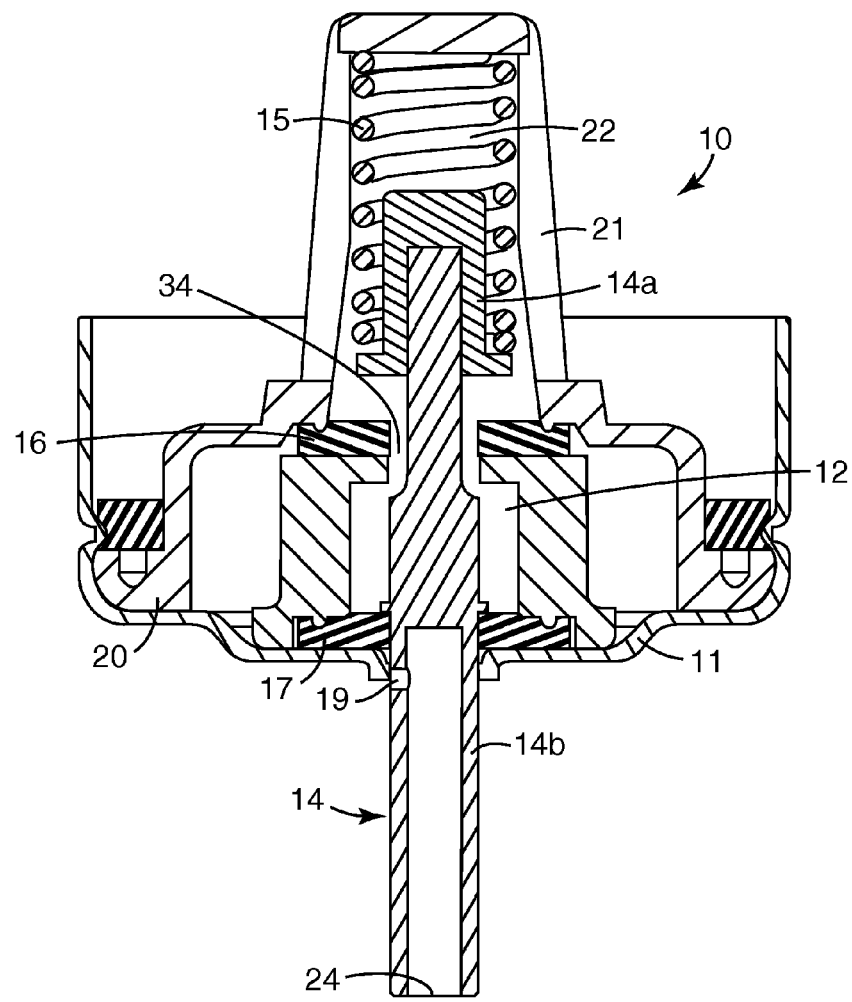

FIG. 3 shows a commercial metered dose valve (10), in its resting position, supplied by Bespak under the trade designation Easifill BK361. Similar to the valve shown in FIG. 1, the valve includes a valve body housing (20) in the form of a spring cage (that defines in part a pre-metering chamber (22)) with, now, two wide slots (21) extending longitudinally the full length of the spring cage and a valve stem (14) made of two components (14a and 14b) passing through the metering chamber (12) and in sliding sealing engagement with the outer diaphragm seal (17). Unlike the valve in FIG. 1, the valve stem, which again is biased outwardly by a compression spring (15), has a narrow diameter in the vicinity of the inner tank seal (16), so that an internal flow channel (34) is provided between the valve stem and the inner seal when the valve at its rest position. The metered dose valve shown in FIG. 3 is a empty-fill type valve in which upon agitation or shaking by the user prior to actuation, the contents of the metering chamber (12) are (re-)dispersed back through the interior of the valve to a formulation chamber (not shown) and upon cessation of agitation or shaking the metering chamber is then charged with re-dispersed formulation passing into the interior of the valve through the pre-metering chamber (22) and the flow channel (34) to the metering chamber. During actuation of the valve, as the valve stem (14) is pushed inwardly, the valve stem comes into sliding sealing engagement with the inner seal (16), thereby sealing off the metering chamber (12) and as the valve stem is yet further displaced inwardly, formulation is allowed to pass from the metering chamber through side hole (19) in the valve stem and through a stem outlet (24) in the valve stem, and subsequently out to the patient typically via an actuator nozzle (not shown).

Figure 4A:
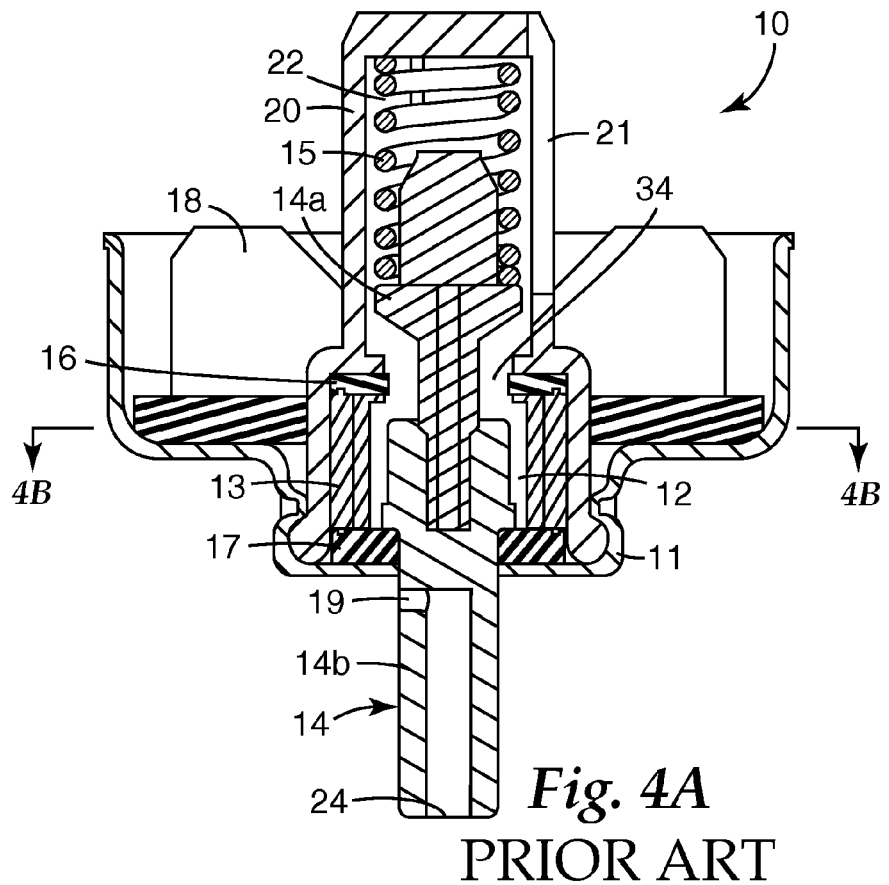
Figure 4B:
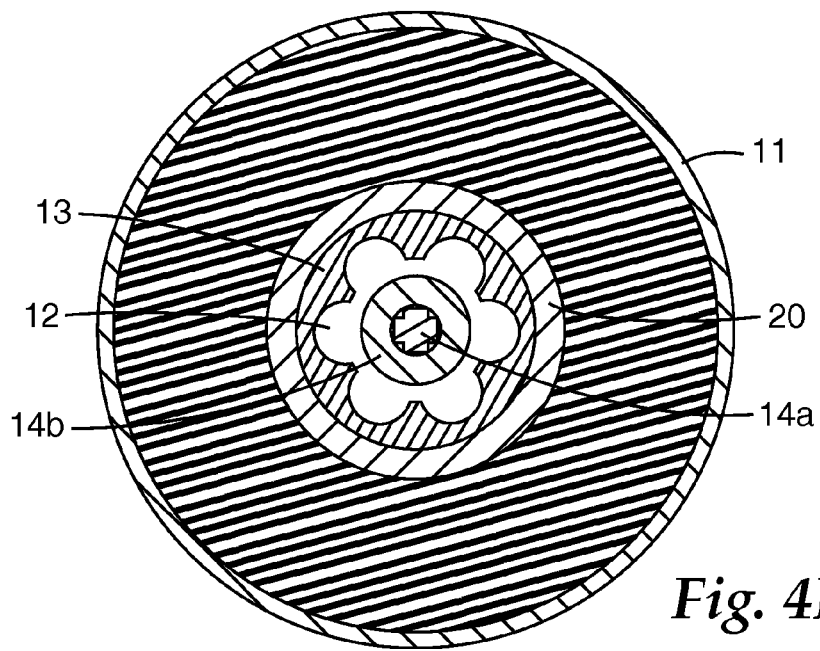

FIG. 4a shows a vertical cross-sectional view of another commercial empty-fill type metered dose valve (10) supplied by Valois under the trade designation DF30 ACT. FIG. 4b shows a horizontal cross-sectional view taken across IVb-IVb of FIG. 4a. The construction and operation of this valve are similar to that described for the empty-fill valve shown in FIG. 3 and for the sake of brevity reference is made here to the aforesaid description. In regard to notable structural differences to valve shown in FIG. 3, it will be recognized that the inner wall of the inner valve body housing (13) is scalloped to provided a lobe-like metering chamber (12) (see FIG. 4b), the valve includes a sloped component (18) about the valve body housing (20) to help direct movement of aerosol formulation into the three elongated slots (21) and the narrow portion of valve stem (14, in particular the upper portion thereof (14a)) near the inner tank seal (16) is cross-shaped in its horizontal cross-section (see FIG. 4b). It will be appreciated that the operation of the valve is the same as that described for the valve of FIG. 3.

Figure 5A:
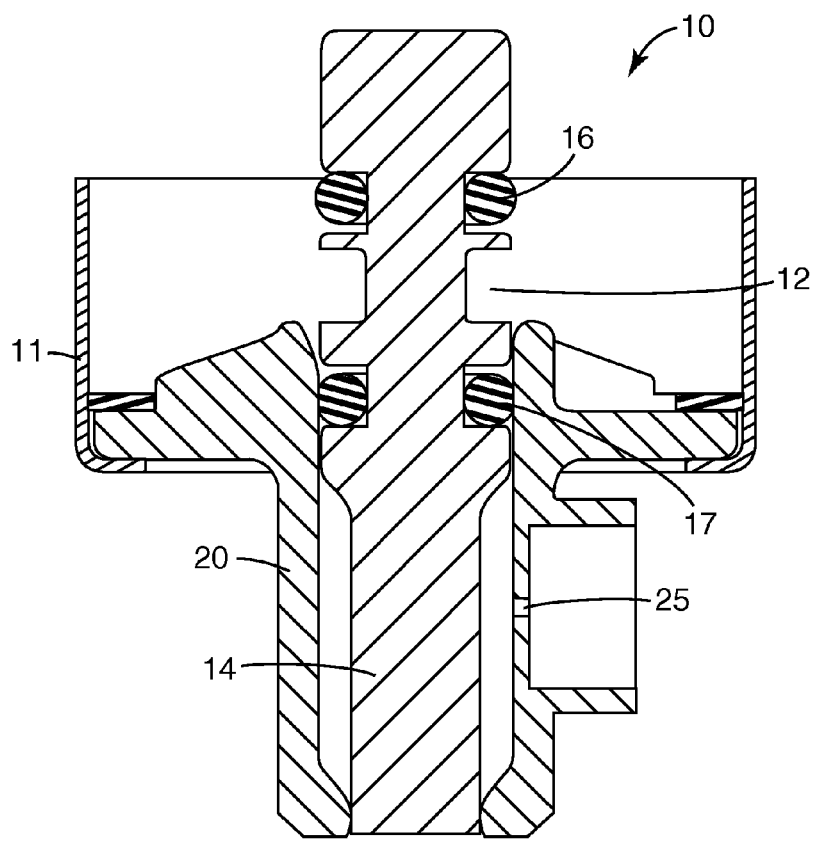
Figure 5B:
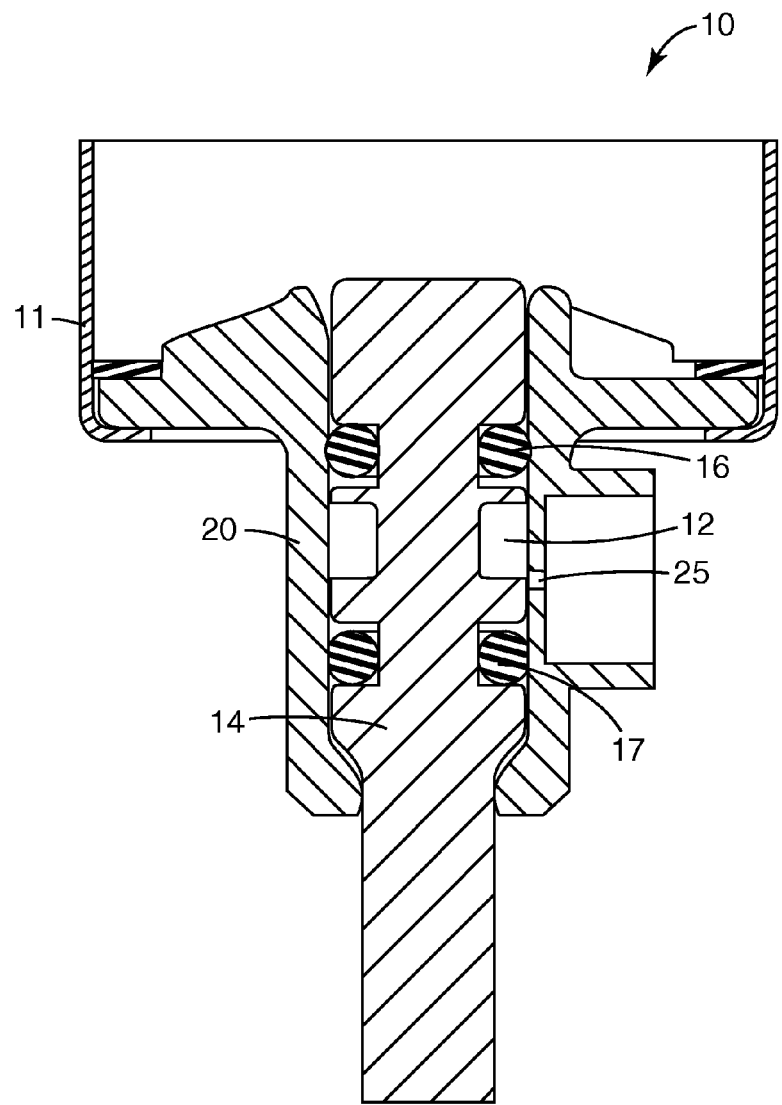
Figure 12A:
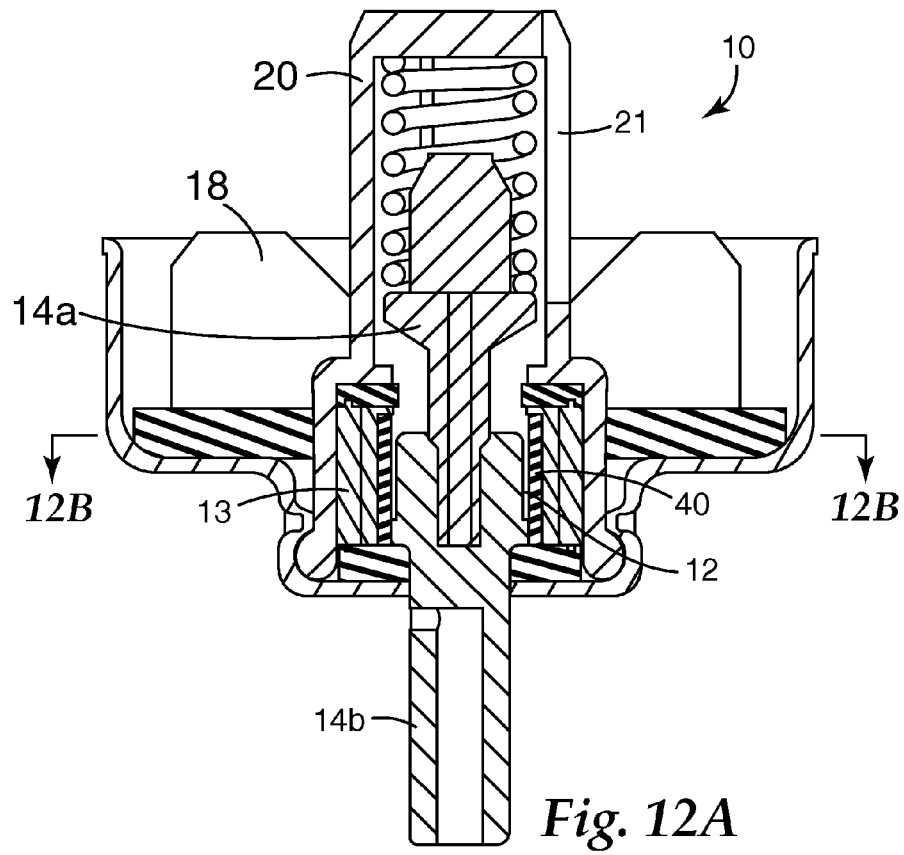
Figure 12B:
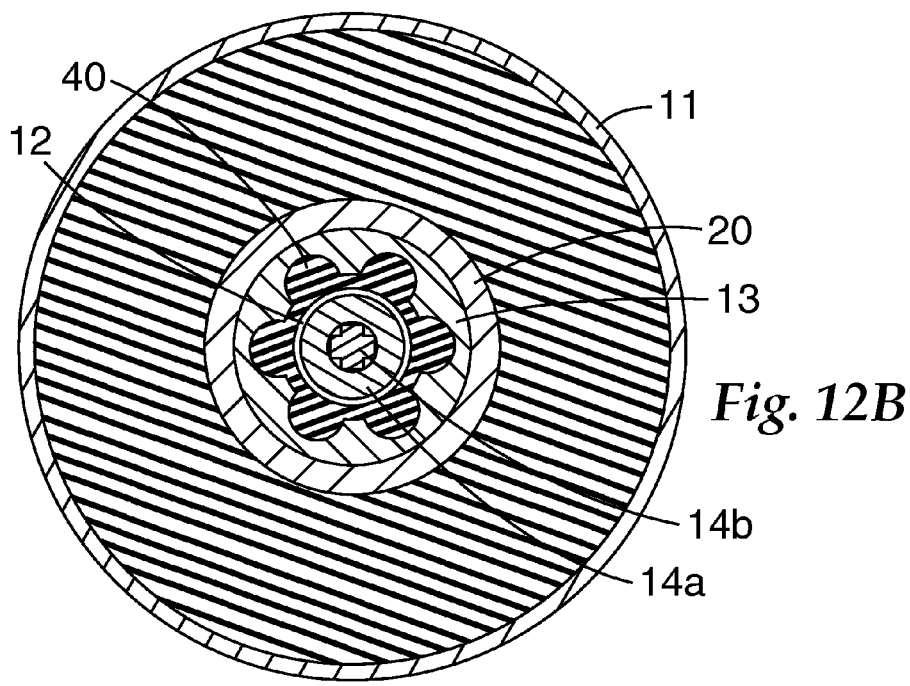

FIGS. 5a and b show a metered dose valve (10) of a type generally similar to that disclosed and described in U.S. Pat. No. 5,772,085 (incorporated herein by reference), in its priming position (FIG. 5a) and its firing/rest position (FIG. 5b). The valve includes a valve body housing (20) and a valve stem (14) that is biased outwardly under the pressure of the aerosol formulation contained within an aerosol container (not shown). The operation of this valve is unlike that for the metered dose valves shown in FIGS. 1 to 4. Here the valve stem (14) is pushed upwards into the formulation chamber (not shown), so that an outer diaphragm seal (17) on the valve stem passes inwardly beyond an outlet (25) provided in the external portion of the valve body housing (20) and then an inner tank seal (16) on the valve stem passes inwardly and disengages from the inner wall of the valve body housing, thus bringing the metering chamber (12) into the formulation chamber so that aerosol formulation can enter the metering chamber (priming position of the valve). Subsequently the valve stem (14) is released moving outwardly so that the inner seal (16) re-engages the inner wall of the valve body housing (20) sealing off the metering chamber (12) and the outer seal (17) then passes outwardly beyond the outlet (25), bringing the metering chamber in communication with the outlet (firing/rest position of the valve), so that the metered dose of aerosol formulation passes through the outlet to the patient. To prevent ingress of moisture, etc. the valve stem is generally moved back to its priming position after a dose has been fired, and consequently similar to the empty-fill valves shown in FIGS. 3 and 4, the content of aerosol formulation in the metering chamber between firings is (re-)dispersed upon agitation or shaking by the user prior to actuation so that the metering chamber is then charged with re-dispersed formulation prior to firing.

FIGS. 6 to 16 show exemplary embodiments in accordance with the present invention. Again for the sake of ease in understanding and comparison, similar components of the respective valves/dispensers are identified with like reference numbers in the Figures.

Referring to FIG. 6 providing a cross-section illustration of an exemplary embodiment of a metered dose valve (10) in accordance with the invention and FIG. 7 providing a cross-section illustration of an exemplary dispenser (100) in accordance with the invention equipped with a valve as shown in FIG. 6, it will be appreciated that in comparison to the inhaler and metered dose valve illustrated in FIG. 1, the metered dose valve includes a porous, fluid permeable, particulate semi-permeable body (40), referred to in the following as "porous body", within the metering chamber (12). (In FIG. 7, for ease in viewing, the cross-hatching representing aerosol formulation has not been included within the interior conduit of the valve.) It will be also appreciated that in comparison to the metered dose valve in FIG. 1, the valve (10) is slightly modified, so that the diameter of the shoulder of the lower component (14*b*) of valve stem (14) (the shoulder near the diaphragm seal (17)) is essentially equal to the diameter of the neighboring portion of the upper component (14*a*) of the valve stem.

Referring to FIG. 1 showing a known inhaler with a dose-retaining-type metered dose valve, it is appreciated for such an inhaler filled with medicament suspension aerosol formulations that sediment or cream, that upon standing for periods of 12 hours, 24 hours or longer that medicament may sediment or cream, as the case may be, out of the metering chamber (depending on the particular suspension formulation and the orientation in which the user has stored the inhaler), by passing back through the valve towards the formulation chamber. For example in the case of the valve shown in FIG. 1, through an annular gap up through the side hole (33*b*), then through the channel (34), second opening (33*a*), pre-metering chamber (22) back to the formulation chamber (3).

Again referring to FIGS. 6 and 7 showing exemplary embodiments of a metered dose valve (10) and a dispenser (100) in accordance with the present invention, respectively, it can be recognized that the porous body (40) is favorably positioned within the metering chamber (12) of the metered dose valve (10). Upon filling of the metering chamber, aerosol formulation and hence medicament particles suspended in the aerosol formulation (4 in FIG. 7; not shown in FIG. 6) are dispersed through the volume of the porous body (40). As mentioned above, it is believed that in these embodiments and other embodiments including a porous body positioned within the metering chamber, the porous body acts to hold medicament particles substantially uniformly dispersed within its volume, limiting and/or preventing any extensive flocculation and/or sedimentation or creaming within the volume of the porous body, thereby limiting and/or preventing loss of dose (e.g. upon standing) from metering chamber and hence facilitating consistency of a metered dose dispensed by the valve.

FIGS. 9, 12 and 15 show alternative exemplary embodiments of metered dose valves which favorably comprise a porous body positioned within the metering chamber. In particular FIG. 9 shows a valve of the type shown in FIG. 3, in its rest position, including a porous body (40) positioned within its metering chamber (12). It will also be appreciated that in comparison to the metered dose valve in FIG. 3, the valve stem has been slightly modified in that the flange (near the diaphragm seal) has been removed. FIG. 12*a* shows a vertical cross-sectional view and FIG. 12*b* shows a horizontal cross-sectional view, taken across XIIb-XIIb of FIG. 12*a*, of another empty-fill type metered dose valve (10) (in its rest position) of the type shown in FIG. 4 including a porous body (40) within the metering chamber (12). It will also be appreciated that the valve shown in FIG. 12 may be favorably modified in that the flange on the valve stem (near the diaphragm seal) could be removed or reduced in size, allowing for a corresponding increase in size of the porous body within the metering chamber. FIGS. 15*a* and *b* show vertical cross-sectional views of a shuttle-type metered dose valve (10) (in its priming position and firing/rest position, respectively) of the type shown in FIG. 5 including a porous body (40) positioned in the metering chamber (12). In such embodiments, upon shaking by the user prior to operation (e.g. actuation) of the valve, medicament suspended in the aerosol formulation is re-dispersed throughout the liquid in the formulation chamber and in the volume of the metering chamber and porous body. After shaking, it is believed that the porous body holding medicament particles substantially uniformly dispersed within its volume favorably limits and/prevents movement of medicament particles out of the metering chamber (loss of dose from the metering chamber) e.g. upon a delay between shaking by the user and firing the valve. Also it is believed that the porous body acting as barrier to any flocculation and/or sedimentation outside the region defined by the porous body so that the porous body favorably limits and/or prevents movement of medicament particles into the metering chamber (an increase in dose in the metering chamber) e.g. upon a delay between shaking by the user and firing the valve. It is to be appreciated that the porous body favorably limits and/or prevents loss of dose from or a change in dose in the metering chamber upon standing so that dose consistency is also facilitated in circumstances where the user does not use the device properly, e.g. forgets or fails to agitate or shake the dispenser prior to valve actuation.

In embodiments favorably including a porous body positioned within the metering chamber, the volume of the region defined by the porous body is desirably greater than 50% of the volume of the metering chamber, more desirably at least 75%, even more desirably at least 85%, and yet even more desirably at least 95% of the volume of the metering chamber. Most desirably the volume of the porous body is essentially equal to or equal to the volume of the metering chamber. Under a volume of the porous body that is essentially equal to the volume of the metering chamber is understood that the porous body fills the volume of the metering chamber as completely as possible while allowing for proper operation of the valve (or conversely without interfering with the proper operation of the valve). For example, referring to the exemplary embodiment shown in FIGS. 15*a* and *b*, it will be appreciated that depending on the selected material of the porous body, e.g. if the porous body is made of a rigid material, it may be desirable or necessary that the outer diameter of the porous body be selected so that there is an appropriate annular gap between the porous body and the inner wall of the valve body housing to ensure proper movement of the valve stem and thus function of the valve. Similarly it will be appreciated that in the exemplary embodiments shown in FIGS. 6, 7, 9 and 12, that it may be favorable to provide an annular gap between the porous body and the valve stem or a relevant portion thereof (in case of the exemplary embodiment shown in FIG. 12) depending on the particular material of the porous body. Also as an additional example, referring to the embodiment shown in FIG. 12, it will be recognized that a porous body including an extension up over the upper shoulder of the lower portion of the valve stem would interfere with the proper operation of the valve, e.g. interfering a sliding sealing engagement between the valve stem and the inner tank seal during operation of the valve.

For embodiments advantageously including a porous body positioned within the metering chamber, generally a single porous body will be positioned within the metering chamber. However two or more porous bodies may be positioned within the metering chamber as desired and/or needed. For example due to the lobe-shaped metering chamber of the embodiment shown in FIG. 12 (see FIG. 12*b*), it may be desirable to position within each of the six lobes of the metering chamber a separate porous body.

In alternative advantageous embodiments, the metered dose valve comprises an internal channel upstream of the metering chamber, in particular an internal channel leading to the metering chamber, and the at least one porous body is positioned within the internal channel.

Figure 8:
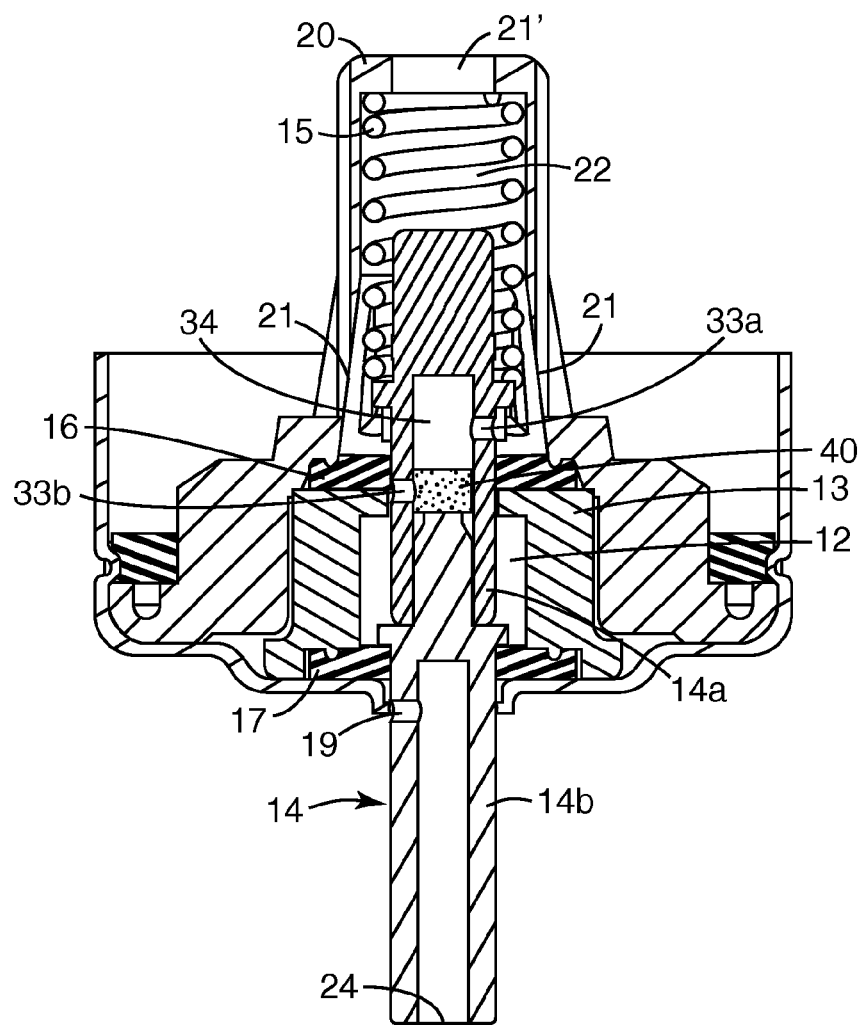
FIGS. 8 to 16 represent schematic cross-sectional views of exemplary embodiments of metered dose valves in accordance with the invention.
Figure 9:
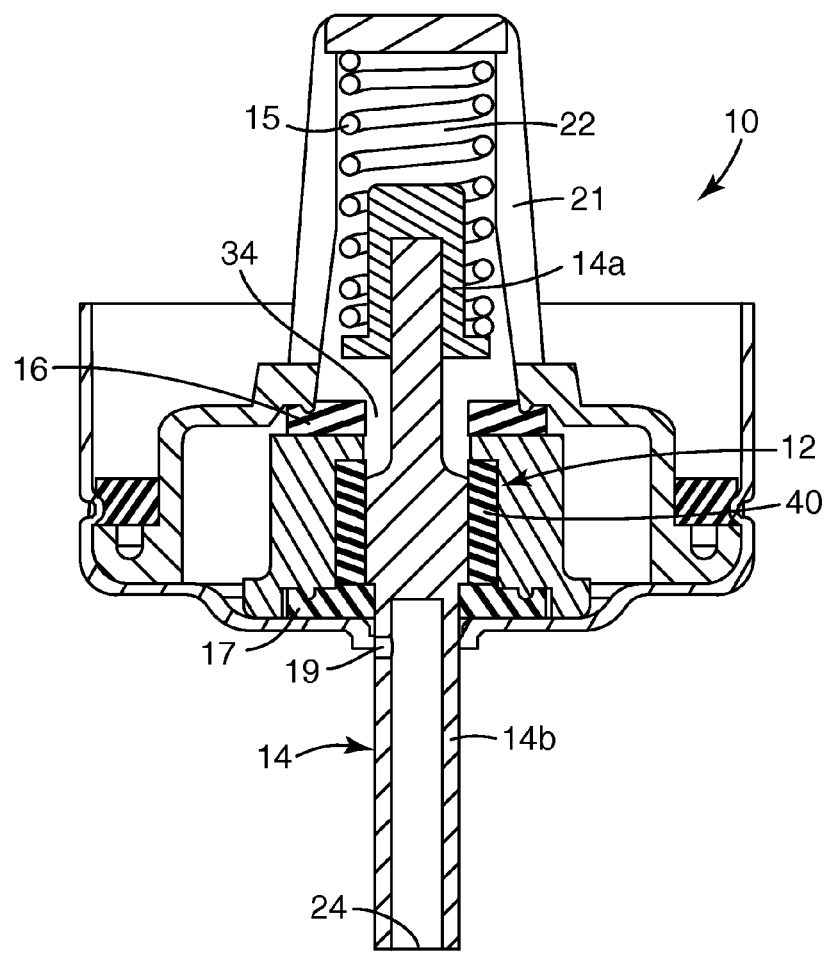

This can be best understood by referring to FIG. 8 showing an exemplary embodiment of a metered dose valve (10) of the type shown in FIG. 1. The exemplary valve shown in FIG. 8 again includes a porous body (40) and here the porous body is positioned within an internal flow channel (34). The flow channel (34) in this valve, which is located in the valve stem (14), connects the pre-metering chamber (22) and the metering chamber (12). The porous body is favorably positioned within the channel directly adjacent to the outlet of the channel leading into the metering chamber, side hole (33*b*). (It will be appreciated that the volume of the porous body (40) may be increased so that the porous body essentially fills the entire volume of the flow channel (34) within the valve stem (14) of the valve illustrated in FIG. 8.)

Figure 13A:
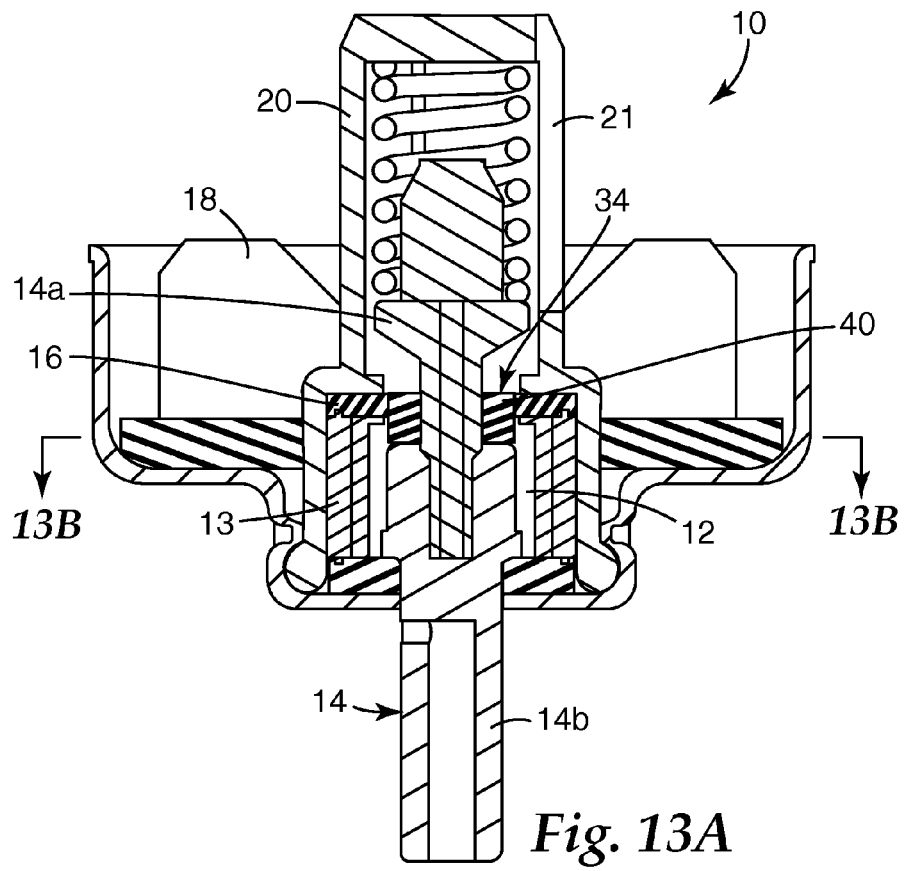
Figure 13B:
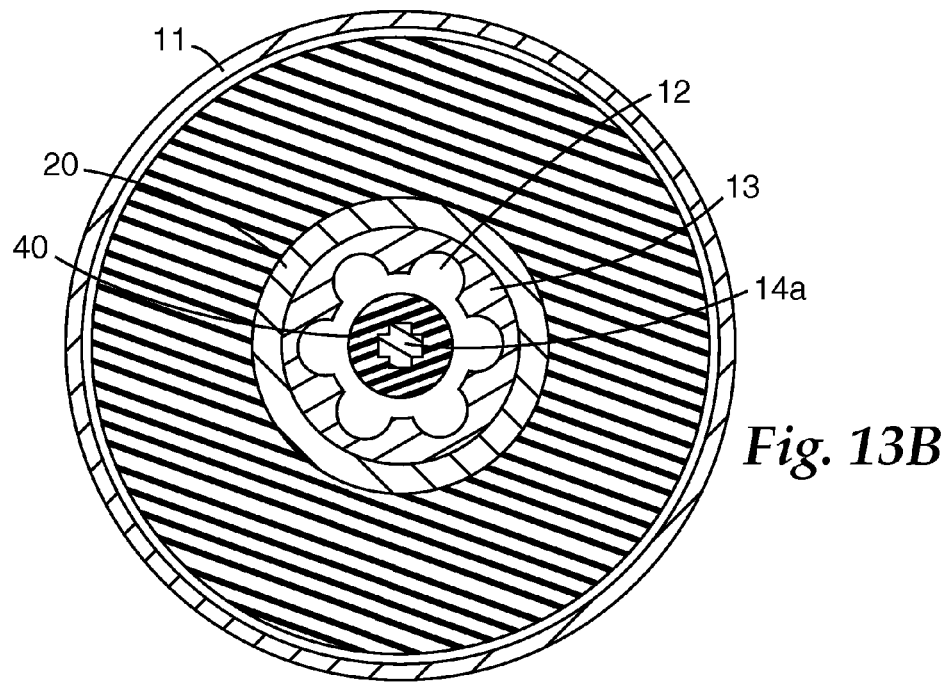

FIG. 13 illustrates another exemplary embodiment of a metered dose valve (10) (in its resting position) having an internal channel (34) in which a porous body (40) is positioned within the channel. FIG. 13*a* provides a vertical cross-sectional view, while FIG. 13*b* shows a horizontal cross sectional view taken across XIIIb-XIIIb of FIG. 13*a*, The valve illustrated in FIG. 13 is an empty-fill valve of the type shown in FIG. 4, in which the porous body (40) is positioned about a portion of the valve stem (14) adjacent to the inner tank seal (16) and the entrance into the metering chamber (12), when the valve is in its rest position. As can be recognized from FIG. 13*a*, when the valve stem (14) is pushed inwardly to actuate the valve, the porous body (40) will move along with the valve stem. It will be recognized that the empty-fill valve of type shown in FIG. 3 can be similarly provided with a porous body within its internal flow channel (34) leading to the metering chamber.

In these embodiments and other embodiments including such an internal channel and a porous body positioned within such channel, it is believed that the porous body acts as barrier, limiting sedimentation or creaming of medicament, as the case may be, into or out of the metering chamber, as the case may, and thus limiting loss of dose from or change of dose in the metering chamber and hence facilitating uniformity of metered doses dispensed by the valve. Accordingly, the porous body is desirably configured and positioned within the internal channel, such that the porous body is near or adjacent to or directly adjacent to the entrance(s) into the metering chamber and/or the exit(s) out of the internal channel (if applicable, when the valve is in its rest or priming position).

It will be appreciated that alternative exemplary embodiments may comprise at least two porous bodies in which at least one porous body is positioned within the metering chamber and at least one porous body within the internal channel. For example, it can be envisioned to provide an embodiment of a metered dose valve of the type shown in FIGS. 6 and 7 including a second porous body positioned within its internal flow channel (34) as illustrated in FIG. 8. The same holds true for empty-fill type valves shown in FIGS. 9 and 12. (See also exemplary embodiment shown in FIG. 11 discussed in more detail below.)

In further, alternative advantageous embodiments, the metered dose valve comprises a pre-metering chamber and the at least one porous body is positioned within the pre-metering chamber.

Figure 10:
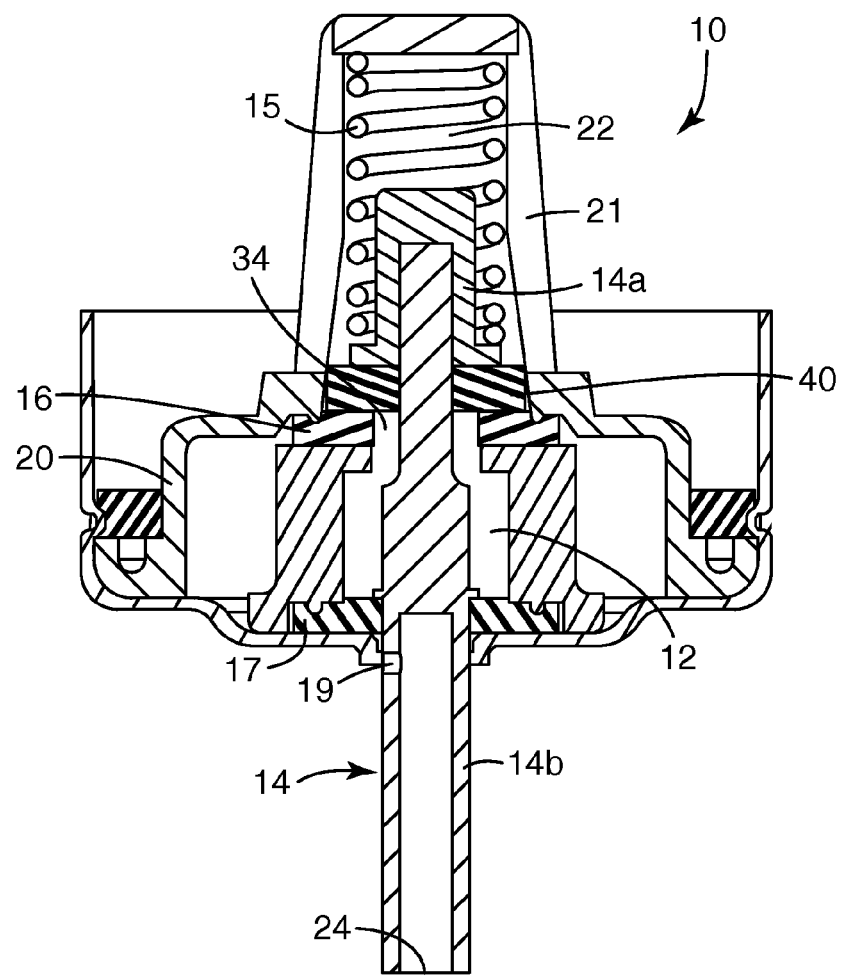
Figure 16:
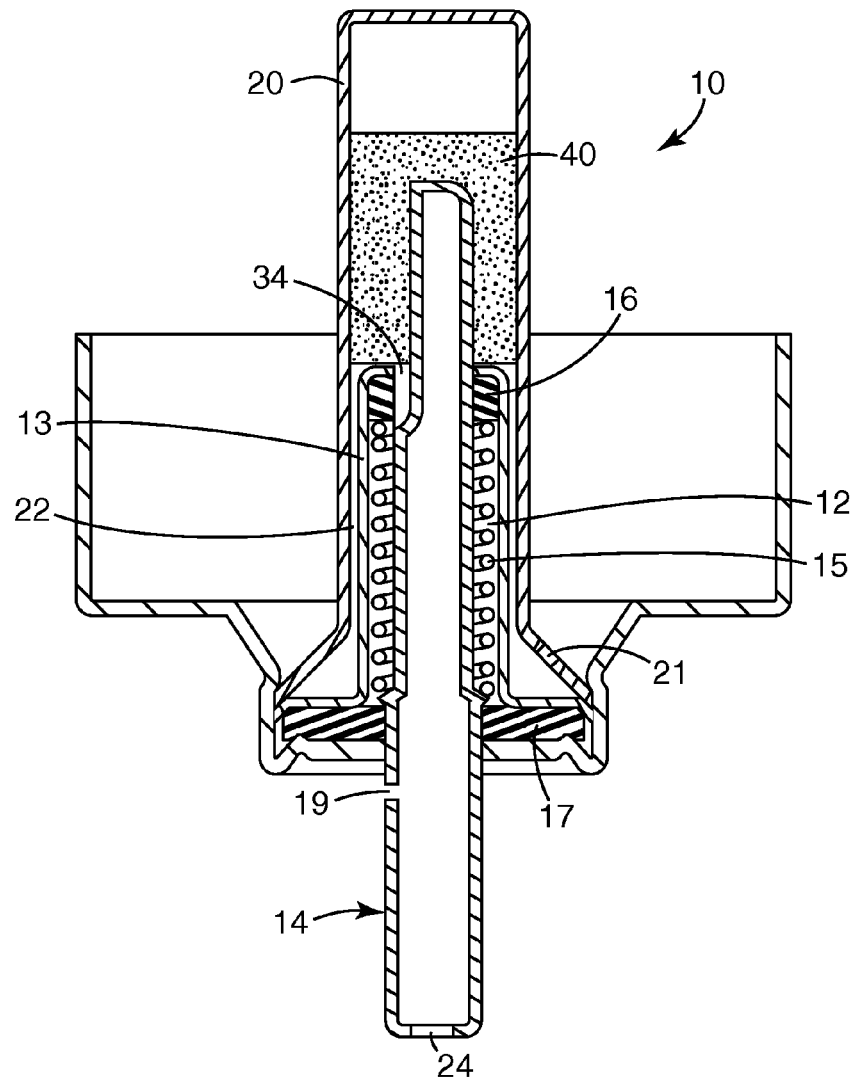
Figure 17:
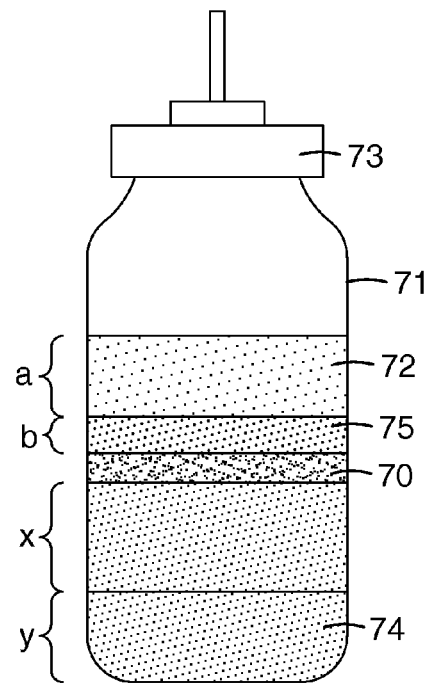
FIG. 17 represents a schematic cross-sectional view of an experimental arrangement useful for rapid pre-screening testing of porous bodies.

This can be best understood by referring to FIG. 16 showing an exemplary embodiment of a metered dose valve (10) of the type shown in FIG. 2. The exemplary valve, which is a dose-retaining type valve and shown in its rest position, comprises a porous body (40) that is positioned within the pre-metering chamber (22). The valve stem is favorably provided with the porous body that is positioned about and affixed to the valve stem (14) adjacent to and extending into the groove (34). FIG. 10 illustrates another exemplary embodiment of a metered dose valve (10) (in its resting position) having a pre-metering chamber (22) in which a porous body (40) is positioned within the pre-metering chamber. The valve illustrated in FIG. 10 is an empty-fill valve of the type shown in FIG. 3, in which the porous body (40) is positioned about a portion of the valve stem (14), just under the upper component of the valve stem (14*a*) and adjacent to the inner tank seal (16) when the valve is in its rest position. In the embodiment shown in FIG. 10, the porous body (40) is favorably affixed to the valve stem, and thus moves together with the valve stem during operation of the valve. Alternatively the porous body may favorably be affixed to the inner wall of the valve body housing (20) so that the porous body remains stationary upon movement of the valve stem. It will be recognized that the empty-fill valve of type shown in FIG. 4 can be similarly provided with a porous body within its pre-metering chamber.

In these embodiments and other embodiments including such an pre-metering chamber and a porous body positioned within such pre-metering chamber, it is believed that the porous body acts as barrier, limiting sedimentation or creaming of medicament, as the case may be, into or out of the metering chamber, as the case may, and thus limiting loss of dose from or change of dose in the metering chamber and hence facilitating uniformity of metered doses dispensed by the valve. Accordingly, the porous body is desirably positioned within the pre-metering chamber directly adjacent to the outlet(s) of the pre-metering chamber towards the metering chamber and/or the entrance(s) of a passageway (e.g. an opening or an internal channel, as the case may be) from the pre-metering chamber to the metering chamber.

Figure 11:
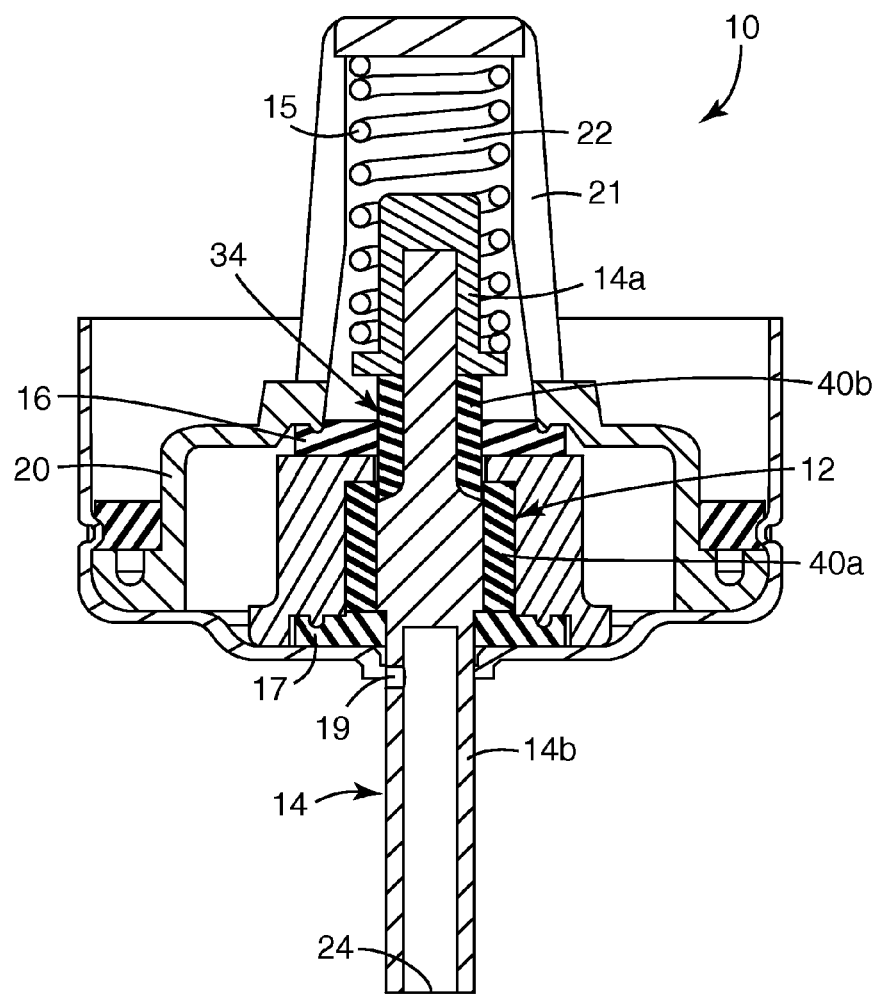
Figure 14:
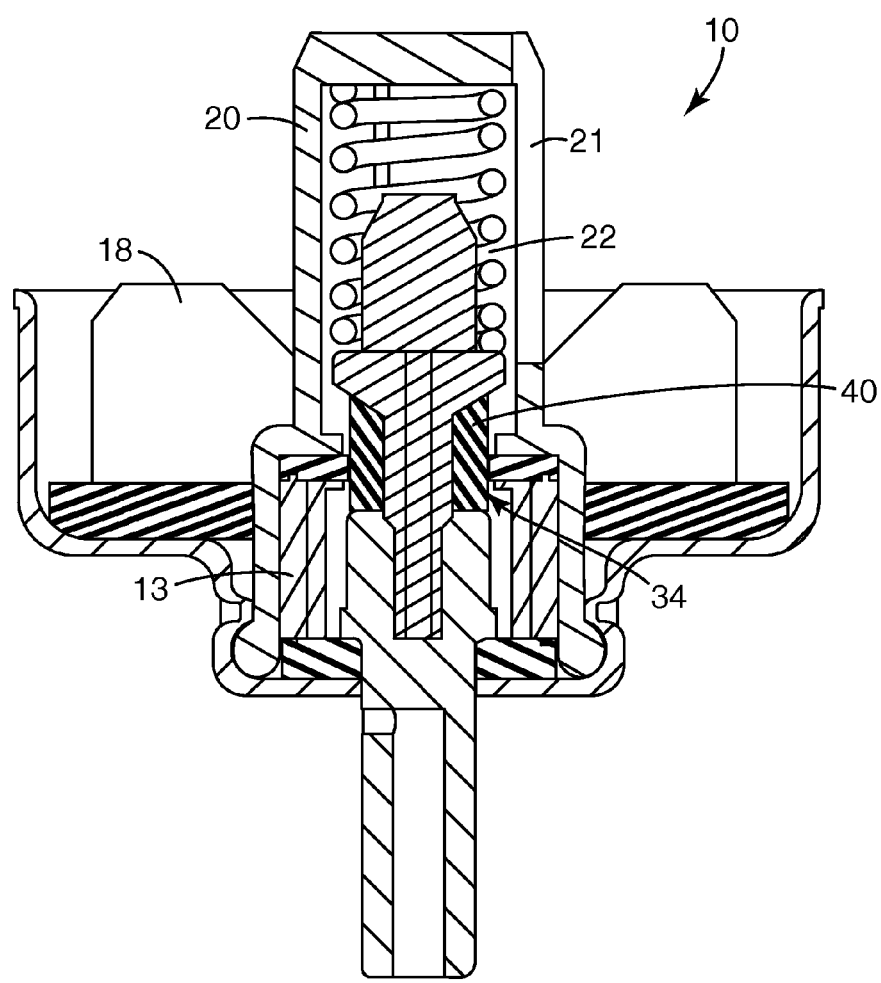

It will be appreciated that alternative exemplary embodiments may comprise a porous body or porous bodies positioned within both the pre-metering chamber and an internal channel leading to the metering chamber, within both the pre-metering chamber and metering chamber or within both chambers and the internal channel between the chambers. For example, FIG. 14 shows an exemplary embodiment having a single porous body (40) positioned within both the pre-metering chamber (22) and the internal channel (34) leading to the metering chamber, while FIG. 11 shows an exemplary embodiment having two porous bodies (40a) and (40b), one positioned within the metering chamber (12) and the other within the pre-metering chamber (22) and internal channel (34) leading to the metering chamber, respectively.

As can be appreciated from the exemplary embodiments described herein, desirably the porous body is positioned within a region or regions of the interior conduit of the metered dose valve, in particular within the metering chamber itself and/or within a portion or portions of the interior conduit upstream from the metering chamber. Through the use of such a porous body or bodies within the interior of the valve, loss of dose from and/or change of dose in the metering chamber can be desirably reduced or substantially eliminated, hence allowing for desirable consistency in dispensed metered doses. Metered dose valves including a porous body as described herein show advantageous uniformity of dosing in through-life dose testing with surprisingly minimal deposition of drug on the surfaces of the porous body.

Also as can be appreciated from the aforesaid exemplary embodiments, the use of a porous body as described herein is advantageous is that it does not require any significant re-design of metered dose valves and/or dispensers (e.g. inhalers) equipped with such metered dose valves. For example existing metered dose valves (and thus existing dispensers (e.g. inhalers)) may be—as such or with only minor structural modifications—readily fitted with such a porous body or bodies.

Depending on the particular metered dose valve and/or valve design, the porous body is generally provided onto a portion of an inner wall of a valve body housing (including if applicable an inner valve body housing) and/or a portion of the valve stem and/or a portion of an inner seal (e.g. diaphragm or tank seal). Depending on the particular metered dose valve, valve design and/or materials used, the porous body may be fitted onto an appropriate portion of the valve (e.g. about a portion of the valve stem) by means of an interference fit, by retaining it captive between two components (e.g. between the valve stem and the inner seal (e.g. see FIG. 14) or within an internal channel formed by two components of a valve stem (e.g. see FIG. 8)) and/or may be alternatively affixed to an appropriate portion or portions of the valve and/or onto an appropriate support component or framework provided on or in the valve by mechanical bonding or fixing, thermal, chemical and/or solvent bonding, more suitably mechanical bonding or fixing, thermal and/or solvent bonding using techniques known in the art. For example a porous body made of a polymeric material may be suitably affixed to a polymeric valve body housing or stem or seal, as applicable, by thermal, chemical or solvent bonding, more suitably thermal or solvent bonding. For example a porous body made of a metallic material may be suitably affixed to a metallic valve body housing or stem, as applicable, by thermal or chemical bonding, more suitably thermal bonding. Mechanical bonding, for instance, may be suitable for affixing a porous body made of a metallic material to a valve component (e.g. valve body housing or stem or seal) made of a polymeric material, for example by embedding an appropriate portion or portions of the porous body into the component to achieve affixation. Generally porous bodies are desirably affixed by mechanical fixing. Suitable methods of mechanical fixing include mechanical interference fits as well as the use of detents, clips, barbs, and other fasteners and other mechanical fastening methods well known to those skilled in the art of affixing small objects and components together.

The particular form or shape of the porous body depends among other things on the particular design of the metered dose valve. Favorably the porous body may be provided as a substantially annular body, a cylindrical body, an open-ended hollow cylindrical body or a hollow cylindrical body with one closed end.

Metered dose valves may be provided with two or more porous bodies. For example, the exemplary embodiment shown in FIG. 11 includes two separate porous bodies, and as already mentioned above, the exemplary embodiment shown in FIG. 12 may be provided six individual porous bodies one in each lobe of the metering chamber instead of a single annular porous body. It will be appreciated that the porous body may be provided as a porous body composite made of two or more porous bodies. For example it can be desirable to layer two or more porous bodies to provide a layered porous body composite, e.g. for purposes of providing enhanced structural stability and/or integrity to the body.

It will be appreciated that porous bodies herein described advantageously include a plurality of pores (e.g. at least 10 pores, but generally a much higher number of pores, e.g. 25 pores or more, 50 pores or more, 100 pores or more, up to very high numbers or even uncountable numbers of pores).

Advantageously, porous bodies have a relatively low relative density; relative density being defined as a percentage of a solid (e.g. the volume of material in a porous body relative to the volume of material in a solid body of base material). Favorably a porous body has a relative density of 50% or less, more favorably 37% or less, even more favorably 25% or less, yet more favorably 15% or less, yet even more favorably 10% or less, and most favorably 5% or less. It will be recognized that relative density is an expression of "openness", and this can also be described as percent void (sometimes also termed percent porosity), percent void being equal to 100 minus relative density. Expressed in terms of percent void, porous bodies advantageously have a relatively high percent void, favorably a percent void of at least 50%, more favorably at least 63%, even more favorably at least 75%, yet more favorably at least 85%, yet even more favorably at least 90% and most favorably at least 95%.

The porous body is fluid permeable. The term "fluid permeable" is generally understood to mean that the body is permeable to liquefied propellant and, if applicable, any other liquid component (e.g. a liquid excipient, such as ethanol), of the aerosol formulation and permeable to propellant vapor and, if applicable, any other gas that may be present in the dispenser, such as residual air, or nitrogen or any other inert gas used to overpressure the product, or water vapor.

The porous body is particulate semi-permeable. The term "particulate semi-permeable" is generally understood to mean that the body is permeable to small particulates, but impermeable to larger particulates in the aerosol formulation. The particular desired particulate selective permeability for the porous body depends in part on the particular aerosol formulation being used, e.g. its drug concentration and/or flocculation behavior. Suitably it has been found that the porous body is generally permeable at least to particulates having a particle size (diameter) of 25 microns or less (e.g. medicament and/or excipient particles typically have a size of 10 microns or less). More suitably the porous body is generally permeable at least to particulates having a particle size of 125 microns or less, even more suitably generally permeable to at least particulates having a particle size of 200 microns or less, and yet even more suitably generally permeable at least to particulates having a particle size of 250 microns or less. Suitably it has been found that the porous body is generally impermeable at least to particulates having a particle size of 2 mm or more. More suitably the porous body is generally impermeable at least to particulates having a particle size of 1 mm or more, even more suitably generally impermeable to at least particulates having a particle size of 900 microns or more, and yet even more suitably generally impermeable at least to particulates having a particle size of 850 microns or more. The particular selective permeability of the porous body can be selected via e.g. dose consistency testing or dose uniformity testing (for example based on a protocol designed to simulate patient use, such as a protocol whereby doses are fired and assayed every 12 or 24 hours), as the case may be, using the particular chosen medicinal suspension aerosol formulation and dispenser (i.e. metered dose valve and aerosol container) fitted with porous bodies to be screened. For preliminary testing it can be useful to perform such testing using aerosol formulation in which the medicament in the formulation has been substituted with Brilliant Blue food dye particles having a similar particle size distribution to that of the intended medicament, because the suspended dye generally behaves similarly to suspended medicament particles, and due to visual color of the dye, assays can be quickly made using photospectrometry. For rapid pre-screening testing of porous bodies, it has also been found useful to examine the properties of the body using an experimental arrangement as shown schematically in FIG. 17. Here a layer of the porous body to be tested (70) is affixed, typically with a suitable adhesive that doesn't affect the formulation, within a clear aerosol (e.g. polyethylene terephthalate (PET) or glass) container (71) towards the center of the container and across the width of the container, the container is filled approximately three fourths full with the relevant aerosol formulation (72) and then sealed with either a metered dose valve (73) or alternatively, with a blank cap. For quick visual assessment the aerosol formulation may again include suspended Brilliant Blue food dye particles in place of suspended medicament particles. Upon shaking to disperse the formulation (72) within the container (71) and to break up any flocs in the formulation, the contents of the container can easily be observed to see whether the aerosol formulation, in particular whether the Brilliant Blue dye particles suspended in the formulation, readily pass through the porous body layer. If ready passage of the dye is not observed, the tested porous body can be eliminated as a potential suitable candidate. If ready passage of the dye is observed, the container (71) can then be placed valve-up as shown in FIG. 17 and allowed to stand. Typically flocculation of the suspended particles can be observed immediately or shortly after cessation of agitation. For a formulation that shows a tendency towards sedimentation, after standing (typically for at least ten minutes) to allow for complete flocculation and sedimentation of the contents, typically a layer of sediment (74) will be observed at the bottom of the container (71) and a second layer of sediment (75) on the upper surface of the porous body layer (70) as shown in FIG. 17. In the event that only a single layer of sediment at the bottom of the container is observed, the tested porous body can be eliminated as a potential suitable candidate. For those tests showing two layers of sediment in which the ratios of the height of the sediment to the height of the rest of the liquid formulation above and below the porous layer (i.e. b/a and y/x, respectively) are nearly equal or equal, the tested porous body can be viewed as a potentially suitable candidate, since such a result indicates that agitated formulation was able to readily pass through the porous body layer but that after cessation of shaking, passage of particulates through the porous body was hindered upon flocculation and/or sedimentation. It will be appreciated that for a formulation that shows a tendency towards creaming, after standing to allow for complete flocculation and creaming of the contents, typically a layer of cream will be observed under the lower surface of the porous body layer as well as a second layer of cream at the formulation/vapor interface. In the event that only a single layer of cream at the formulation/vapor interface is observed, the tested porous body can be eliminated as a potential suitable candidate. For those tests showing two layers of cream, in which the ratios of the height of the cream to the height of the rest of the liquid formulation above and below the porous layer are nearly equal or equal, the tested porous body can be viewed as a potentially suitable candidate. Alternatively or in conjunction with this testing, rapid pre-screening testing can be performed with the relevant medicament aerosol formulation in a similar manner as described for testing with Brilliant Blue food dye, again with an observation of the ratios of the heights of sediment or cream, as the case may be, to the heights of the rest of the liquid formulation above and below the porous layer being nearly equal or equal as an indication of potential suitability of the porous body.

As mentioned above, porous bodies may be suitably made of a metal (e.g. aluminum or aluminum alloy, stainless steel), or a polymer (e.g. polyethers (polyetheretherketone (PEEK)), polyesters, polyurethanes, polyolefins (e.g. polypropylene, polyethylene, or ethylene copolymers (e.g., ethyl vinyl acetate)), polyamides (nylon), polyimides, polyacrylates, polyacetals or fluoropolymers (e.g. ETFE; FEP, PTFE)) or an inorganic composition (e.g. ceramics or glasses) or, if applicable, a combination thereof. The selection may depend on a number of factors, e.g. on the particular metered dose valve, the position of the porous body, its structure, its dimensions and/or whether the porous body will be in sliding contact with another component during operation of the valve. For example in the exemplary embodiment shown in FIG. 8, where the porous body is located within the valve stem in the flow channel between the pre-metering and metering chambers, the porous body may be suitably rigid, e.g. made of a metal or a ceramic. Conversely, for example in the exemplary embodiment shown in FIG. 15, in which the porous body is located in the metering chamber and will come into (and out of) contact and slide pass another component of the valve, in particular the inner wall of the valve body housing, during operation of the valve, the porous body may be desirably compressible and/or resilient, e.g. made of a polymeric resin, so that inter alia the porous body will not be damaged, nor cause damage to the other valve component(s) during operation of the valve Desirably, porous bodies comprise a material having a filamentous or fibrous or ligamentous structure.

Advantageously, porous bodies comprise a material having a relatively low relative density (e.g. the volume of base material in the porous material relative to the volume of base material in a solid block of base material); favorably a relative density of 50% or less, more favorably a relative density of 37% or less, even more favorably 25% or less, yet more favorably 15% or less, yet even more favorably 10% or less, and most favorably 5% or less. Expressed in terms of percent void, porous bodies advantageously comprise a material having a relatively high percent void, favorably a percent void of at least 50%, more favorably at least 63%, even more favorably at least 75%, yet more favorably at least 85%, yet even more favorably at least 90% and most favorably at least 95%.

Porous bodies comprising materials providing tortuous paths for passage of aerosol formulation have been found particularly advantageous for use. Paths for passage may be random and/or ordered, in particular random.

Favorable materials for use include nonwoven webs (e.g. fibrous nonwoven webs), open-cell foams, reticulate open-cell foams as well as non-cellular porous materials providing tortuous paths for passage.

Suitable nonwoven webs include fibrous nonwoven webs known in the art including e.g. wet laid, dry laid (e.g. carded or air laid), spunbond and meltblown, nonwoven webs. Fibrous nonwoven webs that are consolidated (i.e. the fibers of the web being tied together in some way (also known as web bonding)) are generally favored. Consolidated dry laid nonwovens, spunbond nonwovens and meltblown nonwovens have been found to be more suitable, with consolidated dry laid nonwovens generally being most suitable. Fibers of spunbond and meltblown nonwovens are consolidated (typically via entanglement and cohesive sticking) during the spunbond or meltblown process used in making the web. Fibers (staple fibers) of wet laid and dry laid nonwoven webs may be suitably consolidated using techniques known in the art, such as resin bonding (e.g. saturation bonding, gravure printing, screen printing, spray bonding and foam bonding), thermal bonding (e.g. through-air bonding and calendar bonding), solvent bonding or mechanical bonding (e.g. needlepunching, hydroentangling (also known an spunlacing)). Among these techniques thermal and mechanical bonding are generally more favorable in order to avoid inclusion of a resin or the use of solvents.

Fibrous nonwovens generally comprise microfibers. Fibrous nonwovens comprising microfibers having a diameter of at most 70 microns have been found suitable, a diameter of at most 62 microns more suitable, at most 55 microns even more suitable, at most 47 microns yet even more suitable, at most 40 microns most suitable. Fibrous nonwovens comprising microfibers having a diameter of at least 15 microns have been found suitable, a diameter of at least 18 microns more suitable, at least 22 microns even more suitable, and at least 25 microns most suitable. Fibers of spunbond and meltblown may suitably comprise polypropylene, polyester, polyethylene, nylon as well as other polymeric resins suitable for use in spunbond and meltblown processes. Staple fibers for wet-laid and dry laid nonwovens may be natural fiber types and/or synthetic fibers (more suitably synthetic fibers), such as polymeric fibers (e.g. polyester, polypropylene, rayon, acrylic, fluorocarbon (e.g. PTFE or FEP), and other polymeric fibers as well as bicomponent fibers and split fibers), metal-based fibers (e.g. aluminum oxide, stainless steel fibers and others) as well as ceramic or glass fibers.

As mentioned above, favorable materials providing tortuous paths of passage also include open-cell foams, and more suitably reticulate open-cell foams. Such foams may be made of a polymer (e.g. polyethers, polyesters, polyurethanes, polyethylene, polypropylene, ethyl vinyl acetate), metal (e.g. aluminum, aluminum alloy, stainless steel) or an inorganic composition (e.g. ceramics or glasses). Polymeric open-cell and polymeric reticulated open-cell foams have been found to be particularly useful, more particularly such polymeric foams having low densities, e.g. less than 96 kg/m$^3$ (as determined e.g. by ISO 845). Open-cell foams are here generally understood to be materials having interconnected open cells or open cellular regions distributed throughout their volume and having a density lower than that of a solid block of the framework substance. Open-cell foams generally have low relative densities (e.g. 50% or less and more typically 37% or less). Reticulate open cell foams are here generally understood to be materials having a skeletal network of interconnecting open cells or cellular regions substantially free or free of closed cells or closed regions. Reticulate open cell foams generally have very low relative densities (e.g. 25% or less, more typically 15% or less, even more typically 10% or less, most typically 5% or less).

Open cell foams may be formed by methods known in the art. Reticulate open-cell foams may be prepared from an open-cell foam in which the foam is subjected to a process in which residual membranes or cell windows are removed from the foam structure so that a skeletal network remains or alternatively may be prepared through other methods known in the art. For example, reticulate open cell metal or ceramic foams can be prepared using replica processes, e.g. by applying a metal or ceramic coating to a reticulate, interconnected web precursor and then thermally sintering the coating to remove the precursor leaving a metallic or ceramic reticulate open-cell foam. Methods for producing polymeric foams are well known in the art and are for example described in Ullmann's Encyclopedia of Industrial Chemistry, 2000 Electronic Release under the article posted Jun. 15, 2000 entitled "Foamed Plastics" by Weber, De Grave and Roehrl and citations therein. Methods for producing metallic or inorganic (ceramic or glass) foams are well known in the art and are for example described in Ullmann's Encyclopedia of Industrial Chemistry, 2000 Electronic Release under the article posted Jun. 15, 2000 entitled "Metallic Foams" by Weber, Banhart and Baumeister and in KONA, No. 20 (2002) in the article entitled "Synthesis and Fabrication of Inorganic Porous Materials: From Nanometer to Millimeter Size" by Takahashi and Fuji under the sub-section "Synthesis of Spatial Pore". Such methods include e.g. sintering powders/particles (e.g. metal or inorganic powders), solid-gas eutectic solidification (gasars), slurry forming, in-situ solidification or gel-casting, or embedding a matrix of interstices of packed filler particles and subsequently removing the filler particles (e.g. by dissolution). Other suitable methods for making open cell foams or reticulate open cell foams include solid free-form fabrication techniques where three dimensional materials or bodies are produced through additive formation steps e.g. using stereolithography, solid ground curing, selective laser sintering, laminated object manufacturing, three-dimensional printing, shape deposition manufacturing, laser engineered net shaping and fused deposition modeling processes. It will be appreciated that solid free-form fabrication techniques can also be advantageously used to provide porous materials and/or porous bodies for use here, in which the materials and/or bodies have non-cellular structures with open, tortuous paths for passage of aerosol formulation. Returning to open cell foams and reticulate open-cell foams, it has been found that such foams having a nominal pore size as expressed in pores per linear inch (ppi)—as typically specified by foam manufacturers—of at least 10 ppi are generally suitable, at least 20 ppi more suitable, at least 25 ppi even more suitable and at least 30 ppi most suitable. It has been found that such foams having a ppi of 100 ppi or less are generally suitable, at most 90 ppi more suitable, at most 80 ppi even more suitable and at most 70 ppi most suitable. Reticulate open cell foams have been found particularly suitable for use in metered dose valves and/or dispensers as described herein. Examples of suitable reticulate open cell foams include reticulated open-cell polyester based polyurethane, polyester and polyether foams supplied by Customfoams, Deans Road, Old Wolverton, Milton Keynes, MK 12 5NA, UK; reticulate open-cell aluminum, aluminum alloy and vitreous carbon foams supplied by ERG Materials and Aerospace Corporation of Oakland, Calif., USA under the trade designation DUOCEL; and reticulate open-cell stainless steel foams supplied by Porvair plc, Brampton House, 50 Bergen Way, King's Lynn, Norfolk, UK.

Combinations of the aforesaid materials may be advantageously used, for instance in a composite porous body. Depending on the particular composite porous body and/or metered dose valve, porous bodies making up a composite porous body may be held together mechanically and/or partially or fully affixed to one another using suitable known techniques. Preparation of composite porous bodies may be suitably carried out using techniques known in the art, e.g. laminated object manufacturing.

As mentioned above, it has been found that metering valves including a porous body as described herein surprisingly show only a minimal deposition of drug on the surfaces of the porous body. Tendencies for deposition may be favorably further reduced by coating a part of, or all of, the surfaces of the porous body. The provision of such a coating may also be favorable in allowing a greater potential range of useful porous materials and/or to alter the 'extractables' profile of a material. For polymeric porous materials, coatings of cold plasma polymerized monomers may be applied, such as perfluoro-cyclohexane, perfluoro-hexane tetrafluoroethylene (TFE), trifluoroethylene, vinylidene fluoride, vinyl fluoride, or fluoroacrylates as described in WO 98/58117, incorporated herein by reference, siloxanes, silazanes, alkoxysilanes, or silane derivatives of perfluoropolyoxyalkanes, each being applied by methods well known in the art. The plasma may be formed by breaking down polymers such as PTFE or other substances that produce $CF_2$ radicals, e.g. by hot filament pyrolysis of hexafluoropropylene. Alternatively, a coating of a paraxylylene or derivative may be polymerized in-situ by vapor deposition of the monomer as described in U.S. Pat. No. 3,379,803. For metal and/or inorganic (e.g. ceramics or glasses) porous materials, the above coatings are also suitable. Fluoropolymer coatings comprising PTFE, FEP, PFA, ETFE or PTFE/PFA, with or without a non-fluoropolymer component, such as Teflon® industrial coatings available from DuPont Fluoroproducts, Wilmington, Del., USA, may be suitable. Coatings as described in WO 2001/64524, WO 2001/64273, WO 2001/64274, or WO 2001/64275, may be applied. Alternatively, coatings with a reactive head group selected from carboxylic acids, phosphonic acids and sulphonic acids may be employed, such as 11-perfluoro-n-butyl undecyl phosphonic acid (as disclosed in our co-pending U.S. provisional patent application No. 60/785,823).

Metered dose valves and/or dispensers in accordance with the present invention as disclosed herein, may be advantageously utilized as part of or as dispensers for the administration of medicament through oral, transmucosal (e.g. buccal, sublingual), vaginal, rectal, ocular or aural delivery. Metered dose valves and/or dispensers disclosed herein are particularly suited for delivering medicaments by inhalation to a patient. Accordingly, metered dose valves and/or dispensers described herein are particularly suitable for use in or as metered dose inhalers.

For delivery by inhalation, suitable medicaments include any drug or drugs combination that may be administered by inhalation and that can be provided in the form of particles suitable for suspension in liquefied propellant, in particular liquefied HFA 134a and/or HFA 227.

Drug particles used in the dispensers described herein generally have a mass median particle diameter of typically 10 microns or less. More suitably, said mass median diameter is 7 microns or less, even more suitably 5 microns or less, and most suitably said mass median diameter is in the range 1 to 3 microns, with at least 90% by mass of the particles having diameters below 5 microns. Drug particles may be micronized, e.g. by using a fluid energy mill driven by compressed air, such as shown in 'Drug Delivery to the Respiratory Tract' ed. D. Ganderton and T. Jones, publ. Ellis Horwood, Chichester (1987) pages 89-90, or by repeated stepwise millings or by use of a closed loop milling system.

Suitable drugs include those for the treatment of respiratory disorders, e.g., bronchodilators, anti-inflammatories (e.g. corticosteroids), anti-allergics, anti-asthmatics, anti-histamines, and anti-cholinergic agents. Other drugs such as anorectics, anti-depressants, anti-hypertensive agents, anti-neoplastic agents, anti-tussives, anti-anginals, anti-infectives (e.g. antibacterials, antibiotics, anti-virals), anti-migraine drugs, anti-peptics, dopaminergic agents, analgesics, beta-adrenergic blocking agents, cardiovascular drugs, hypoglaecemics, immunomodulators, lung surfactants, prostaglandins, sympathomimetics, tranquilizers, steroids, vitamins, sex hormones, vaccines and other therapeutic proteins and peptides may also be employed for delivery by inhalation.

Exemplary drugs which may be employed for delivery by inhalation include but are not limited to: albuterol, terbutaline, fenoterol, metaproterenol, isoproterenol, isoetharine, bitolterol, epinephrine, tulobuterol, bambuterol, reproterol, adrenaline, ipratropium, oxitropium, tiotropium, beclomethasone, betamethasone, flunisolide, budesonide, mometasone, ciclesonide, rofleponide, aminophylline, dyphylline, theophylline, cromolyn sodium, nedocromil sodium, ketotifen, azelastine, ergotamine, cyclosporine, salmeterol, fluticasone, formoterol, procaterol, indacaterol, TA2005, omalizumab, montelukast, zafirlukast, betamethasone sodium phosphate, dexamethasone, dexamethasone sodium phosphate, dexamethasone acetate, prednisone, methylprednisolone acetate, zileuton, insulin, atropine, prednisolone, benzphetamine, chlorphentermine, amitriptyline, imipramine, clonidine, actinomycin c, bromocriptine, buprenorphine, pentamidine, calcitonin, leuprolide, alpha-1-antitrypsin, interferons, propranolol, lacicortone, triamcinolone, dinoprost, xylometazoline, diazepam, lorazepam, folic acid, nicotinamide, clenbuterol, ethinyloestradiol, levonorgestrel, and pharmaceutically acceptable salts and esters thereof such as albuterol sulfate, formoterol fumarate, salmeterol xinafoate, beclomethasone dipropionate, triamcinolone acetonide, fluticasone propionate, tiotropium bromide, leuprolide acetate and mometasone furoate.

Further drugs that may also be delivered by inhalation include but are not limited to aspirin, acetaminophen, ibuprofen, naproxen sodium, buprenorphine hydrochloride, propoxyphene hydrochloride, propoxyphene napsylate, meperidine hydrochloride, hydromorphone hydrochloride, morphine sulfate, fentanyl citrate, oxycodone hydrochloride, codeine phosphate, dihydrocodeine bitartrate, pentazocine hydrochloride, hydrocodone bitartrate, levorphanol tartrate, diflunisal, diamorphine, trolamine salicylate, methadone hydrochloride, nalbuphine hydrochloride, nalorphine, tetrahydrocannabinol, mefenamic acid, butorphanol tartrate, choline salicylate, butalbital, phenyltoloxamine citrate, diphenhydramine citrate, methotrimeprazine, cinnamedrine hydrochloride, meprobamate, ergotamine tartrate, propanolol hydrochloride, isometheptene mucate, dichloralphenazone, sumatriptan, rizatriptan, zolmitriptan, naratriptan, eletriptan, barbiturates (e.g., pentobarbital, pentobarbital sodium, secobarbital sodium), benzodiazapines (e.g., flurazepam hydrochloride, triazolam, tomazeparm, midazolam hydrochloride, lorazepam, buspirone hydrochloride, prazepam, chlordiazepoxide hydrochloride, oxazepam, clorazepate dipotassium, diazepam, temazepam), lidocaine, prilocaine, xylocaine, beta-adrenergic blockers, calcium channel blockers (e.g., nifedipine, diltiazem hydrochloride, and the like), nitrates (e.g., nitroglycerin, isosorbide dinitrate, pentaerythritol tetranitrate, erythrityl tetranitrate), hydroxyzine pamoate, hydroxyzine hydrochloride, alprazolam, droperidol, halazepam, chlormezanone, haloperidol, loxapine succinate, loxapine hydrochloride, thioridazine, thioridazine hydrochloride, thiothixene, fluphenazine hydrochloride, fluphenazine decanoate, fluphenazine enanthate, trifluoperazine hydrochloride, chlorpromazine hydrochloride, perphenazine, lithium citrate, prochlorperazine, lithium carbonate, bretylium tosylate, esmolol hydrochloride, verapamil hydrochloride, amiodarone, encamide hydrochloride, digoxin, digitoxin, mexiletine hydrochloride, disopyramide phosphate, procainamide hydrochloride, quinidine sulfate, quinidine gluconate, quinidine polygalacturonate, flecainide acetate, tocainide hydrochloride, lidocaine hydrochloride, phenylbutazone, sulindac, penicillamine, salsalate, piroxicam, azathioprine, indomethacin, meclofenamate sodium, gold sodium thiomalate, ketoprofen, auranofin, aurothioglucose, tolmetin sodium, colchicine, allopurinol, heparin, heparin sodium, warfarin sodium, urokinase, streptokinase, altoplase, aminocaproic acid, pentoxifylline, empirin, ascriptin, valproic acid, divalproate sodium, phenyloin, phenyloin sodium, clonazepam, primidone, phenobarbitol, phenobarbitol sodium, carbamazepine, amobarbital sodium, methsuximide, metharbital, mephobarbital, mephenyloin, phensuximide, paramethadione, ethotoin, phenacemide, secobarbitol sodium, clorazepate dipotassium, trimethadione, ethosuximide, doxepin hydrochloride, amoxapine, trazodone hydrochloride, amitriptyline hydrochloride, maprotiline hydrochloride, phenelzine sulfate, desipramine hydrochloride, nortriptyline hydrochloride, tranylcypromine sulfate, fluoxetine hydrochloride, doxepin hydrochloride, imipramine hydrochloride, imipramine pamoate, nortriptyline, amitriptyline hydrochloride, isocarboxazid, desipramine hydrochloride, trimipramine maleate, protriptyline hydrochloride, hydroxyzine hydrochloride, diphenhydramine hydrochloride, chlorpheniramine maleate, brompheniramine maleate, clemastine, azelastine, cyproheptadine hydrochloride, terfenadine citrate, clemastine, triprolidine hydrochloride, carbinoxamine maleate, diphenylpyraline hydrochloride, phenindamine tartrate, lamivudine, abacavir, acyclovir, gancyclovir, valganciclovir, cidofovir, foscarnet, azatadine maleate, tripelennamine hydrochloride, dexchlorpheniramine maleate, methdilazine hydrochloride, trimprazine tartrate, trimethaphan camsylate, phenoxybenzamine hydrochloride, pargyline hydrochloride, deserpidine, diazoxide, guanethidine monosulfate, minoxidil, rescinnamine, sodium nitroprusside, rauwolfia serpentina, alseroxylon, phentolamine mesylate, reserpine, calcitonin, parathyroid hormone, acitretin, amikacin sulfate, aztreonam, benzydamine, calcipotriol, chloramphenicol, chloramphenicol palmitate, chloramphenicol sodium succinate, ciprofloxacin hydrochloride, clindamycin hydrochloride, clindamycin palmitate, clindamycin phosphate, efalizumab, metronidazole, metronidazole hydrochloride, gentamicin sulfate, lincomycin hydrochloride, tobramycin sulfate, tacrolimus, vancomycin hydrochloride, polymyxin B sulfate, colistimethate sodium, colistin sulfate, tetracycline, griseofulvin, keloconazole, interferon gamma, zidovudine, amantadine hydrochloride, ribavirin, acyclovir, pentamidine e.g. pentamidine isoethionate, cephalosporins (e.g., cefazolin sodium, cephradine, cefaclor, cephapirin sodium, ceftizoxime sodium, cefoperazone sodium, cefotetan disodium, cefutoxime axotil, cefotaxime sodium, cefadroxil monohydrate, ceftazidime, cephalexin, cephalothin sodium, cephalexin hydrochloride monohydrate, cefamandole nafate, cefoxitin sodium, cefonicid sodium, ceforanide, ceftriaxone sodium, ceftazidime, cefadroxil, cephradine, cefuroxime sodium, and the like), penicillins (e.g., ampicillin, amoxicillin, penicillin G benzathine, cyclacillin, ampicillin sodium, penicillin G potassium, penicillin V potassium, piperacillin sodium, oxacillin sodium, bacampicillin hydrochloride, cloxacillin sodium, ticarcillin disodium, azlocillin sodium, carbenicillin indanyl sodium, penicillin G potassium, penicillin G procaine, methicillin sodium, nafcillin sodium, and the like), erythromycins (e.g., erythromycin ethylsuccinate, erythromycin, erythromycin estolate, erythromycin lactobionate, erythromycin siearate, erythromycin ethylsuccinate, and the like), tetracyclines (e.g., tetracycline hydrochloride, doxycycline hyclate, minocycline hydrochloride, GM-CSF, ephedrine, pseudoephedrine, ammonium chloride, androgens (e.g., danazol, testosterone cypionate, fluoxymesterone, ethyltostosterone, testosterone enanihate, methyltestosterone, fluoxymesterone, testosterone cypionate), estrogens (e.g., estradiol, estropipate, conjugated estrogens), progestins (e.g., methoxyprogesterone acetate, norethindrone acetate), levothyroxine sodium, human insulin, purified beef insulin, purified pork insulin, glyburide, chlorpropamide, glipizide, tolbutamide, tolazamide, rosiglitazone, pioglitazone, troglitazone, clofibrate, dextrothyroxine sodium, probucol, lovastatin, rosuvastatin, niacin, DNase, alginase, superoxide dismutase, lipase, calcitonion, alpha-1-antitrypsin, interferons, sense or anti-sense nucleic acids encoding any protein suitable for delivery by inhalation, erythropoietin, famotidine, cimetidine, ranitidine hydrochloride, omeprazole, esomeprazole, lanzoprazole, meclizine hydrochloride, nabilone, prochlorperazine, dimenhydrinate, promethazine hydrochloride, thiethylperazine, scopolamine, sildenafil, vardenafil, cilomilast, imiquimod or resiquimod. Where appropriate, these drugs may be delivered in alternative salts forms.

As mentioned above, metered dose valves and/or dispensers described herein are particularly suitable for use with dispensing aerosol formulations comprising medicament particles suspended in liquefied propellant, in particular HFA 134a and/or HFA 227 as propellant, optionally in combination with one or more excipients.

Excipients may include for example, surfactants, co-solvent and/or suspending aids.

Suitable surfactants include those disclosed in EP 372777, GB 837465 and GB 994734, each incorporated herein by reference. Span 85, oleic acid and/or lecithin are commonly used in medicinal aerosol formulations. Other suitable surfactants for use in medicinal aerosol formulations include HFA-soluble fluorocarbons such as those referred to in WO 91/11173, GB 2263064, each incorporated herein by reference, as well as polyethyleneoxide, polyoxyethylene-oxypropylene block copolymers such as members of the Synperonic PE series (Croda International plc), polyoxypropylenes, polyoxyethylene-polyoxypropylene-ethylenediamine copolymers such as members of the Synperonic T series, castor oil ethoxylates such as Alakasurf CO-40, acetylated monoglycerides (e.g. Myvacet 9-40 or 9-45 from Farma International), polyvinyl pyrrolidone, polyvinylacetate, polyvinyl alcohol, polymers of acrylic acid, methacrylic acid and copolymers thereof, polyoxyethylene glyceryl trioleate (TagatTO), Polyoxyethylene glyceryl monooleate (TagatO or TagatO2 from Degussa), Diol-diacids such as those disclosed in WO 94/21228, incorporated herein by reference, oligolactic acid and derivatives thereof, such as those disclosed in WO 94/21229, incorporated herein by reference, functionalized PEGs such as those disclosed in WO 2003/059317, incorporated herein by reference, amide-ester excipients such as those disclosed in WO 2003/059331, incorporated herein by reference, Propoxylated PEG (Antarox 31R1 from Solvay), polyoxyethylene glycerol esters such as those disclosed in U.S. Pat. No. 5,536,444, incorporated herein by reference, protective colloids such as those described in WO 95/15151, incorporated herein by reference, glyceryl triesters, capr(yl)ic diglyceryl succinates (e.g. Miglyol 829 from Condea Chemie GmbH), Vitamin E acetate, tocopherol (Vitamin E), polyglycolized polyglyceride (e.g. Labrafac Hydro WL 1219 from Gattefosse, Gennevilliers, France), polypropylene glycol, polyethylene glycol e.g. PEG300, aminoacids or derivatives such as disclosed in U.S. Pat. No. 6,136,294 incorporated herein by reference, and other surfactants in the same chemical family as the above but differing in chain length of alkyl or polyalkoxy groups.

Suitable co-solvents may include ethanol, propanol, isopropanol, and other alcohols, glycerol, polyethylene glycol 400, propylene glycol, decanol, sorbitol, mannitol, lactitol, maltitol, glycofurol, dipropylene glycol, propylene glycol diesters of medium chain fatty acids (e.g. Miglyol 840), triglyceride esters of medium chain fatty acids (e.g. Miglyol 810, 812), perfluorocyclobutane, perfluoropentane, perfluorodimethylcyclobutane, menthol, eucapyptus oil, propylene glycol monolaurate (Lauroglycol), diethylene glycol monoethyl ester (Transcutol), isopropyl myristate, saturated hydrocarbons in liquid form and essential oils. Ethanol is commonly used in medicinal aerosol formulations.

Suitable suspending aids may include lactose, glucose, sucrose, D(+)trehalose, as well as their various hydrates, anomers and/or enantiomers, other saccharides such as D-galactose, maltose, D(+)raffinose pentahydrate, sodium saccharin, polysaccharides such as starches, modified celluloses, dextrins, dextrans, DL-alanine, other aminoacids or derivatives such as disclosed in U.S. Pat. No. 6,136,294 incorporated herein by reference, ascorbic acid, sodium sulphate, cetyl pyridinium chloride or bromide other salts e.g. sodium chloride, calcium carbonate, sodium tartrate, calcium lactate, or other organic compounds e.g. urea or propyliodone.

As mentioned above, suspension formulations including HFA 134a typically show a tendency towards sedimentation due to the relatively low density of HFA 134a, while suspension formulations including HFA 227 can show a tendency towards creaming due to the relatively high density of HFA 227. Suspension formulations including HFA 227 as the only propellant most often have a tendency to cream, again due to the relatively high density of the propellant, and for this reason dispensers and/or metered dose valves including a porous body as herein described are advantageous for use with such suspension formulations. Examples of suspension formulations comprising medicament and HFA 227 as the only propellant include such suspension formulations in which the medicament is sodium cromoglycate; nedocromil, a combination of sodium cromoglycate and reproterol, procaterol, a combination of isoprenaline, atropine methyl bromide and dexamethasone.

Suspension formulations consisting essentially of (or more particularly consisting of) medicament and HFA 134a and/or HFA 227 often show a pronounced tendency to sediment or cream. This holds particularly true when HFA134a or HFA227 is used as the only propellant. The commercial metered dose inhalers marketed by GlaxoSmithKline under the trade designations VENTOLIN, FLOVENT (HFA), and SERETIDE provide examples of suspension formulations consisting of medicament and HFA 134a (the medicament being albuterol sulfate, fluticasone proprionate, and a combination of salmeterol xinafoate and fluticasone proprionate in these products, respectively). Thus the dispensers and/or metered dose valves including a porous body as herein described are especially advantageous for use in dispensing such medicament suspension aerosol formulations.

This also holds true for suspension formulations comprising (more particularly consisting essentially of, even more particularly consisting of) medicament, HFA 134a and/or HFA 227 and low amounts of ethanol (e.g. 5% or less by weight of the formulation), because such formulations generally show a greater tendency to coarser flocculation and thus a greater tendency towards sedimentation or creaming problems. Also suspension formulations including low levels of surfactant (for example sorbitan trioleate, oleic acid or soya lecithin) at less than 0.2% by weight of the formulation, also exhibit a tendency towards coarse flocculation. Hence dispensers and/or metered dose valves including a porous body as described herein are also especially advantageous for use in delivering suspension formulations comprising (more particularly consisting essentially of, even more particularly consisting of) medicament, HFA 134a and/or HFA 227 and less than 0.2% by weight of surfactant.

Dispensers and/or metered dose valves including a porous body as herein described are also especially advantageous for use in dispensing suspension formulations including a combination of drugs or including a potent drug (i.e. a drug where the typical therapeutic dose is 20 micrograms or less), because these formulations often pose special problems, e.g. inconsistent dosing as the result of density differences between the drugs, or because of potentially deleterious effects associated with undesired elevated concentration of potent drug, respectively. Examples of suspension formulations including a combination of drugs include those named above, as well as suspension formulations comprising HFA 134a and/or HFA 227 and a combination of formoterol (e.g. formoterol fumarate) with fluticasone (e.g. fluticasone proprionate), budesonide, or mometasone (e.g. mometasone furoate). Examples of suspension formulations including a potent drug include suspension formulations comprising HFA 134a and/or HFA 227 and a medicament selected from the group formoterol (e.g. formoterol fumarate), salmeterol (e.g. salmeterol xinafoate); procaterol (e.g. procaterol hydrochloride), indacaterol, TA2005, ipratropium (e.g. ipratropium bromide), tiotropium (e.g. tiotropium bromide) as well as, as applicable, pharmaceutically acceptable salts, esters, solvates and other physiologically functional derivatives thereof.

As will be appreciated from the aforesaid discussion, metered dose valves and/or dispensers in accordance with the present invention are particularly favorable for use with suspension aerosol formulations which are often problematic in regard to consistency of dosing. Furthermore, aerosol formulations that may be discarded or may have been discarded during product development due to dose consistency issues may be acceptable for use in conjunction with, metered dose valves and/or dispensers herein described. Thus metered dose valves and/or dispensers described here may desirably enhance product and/or aerosol formulation development options.

Example

Materials Used

1. Valve

In the following example, 50 µl machined plastic release-to-fire shuttle-type metering valves (of a generally similar type to that disclosed in U.S. Pat. No. 5,772,085 FIG. 1a) having a design generally as shown in FIG. 5 herein were used.

2. Material for Porous, Fluid Permeable, Particulate Semi-Permeable Body

An open cell reticulated polyester-based polyurethane foam commercially available under the trade designation CFS R80 from Custom Foams, Deans Road, Old Wolverton, Milton Keynes MK12 5NA, U.K was used; the foam having 80 pores per inch (which approximately corresponds to a pore size of 0.010 inch or 0.254 mm), 18-21 cells/cm and a density (ISO 845) of 26-32 kg/m$^3$. Based on a theoretical full density for a solid block of polyester-based polyurethane base material (1140 kg/m$^3$), the foam has a corresponding relative density of about 2.3 to about 2.8%. The foam is reported to have a compression load deflection (ISO 3386/1) of 2.0 to 4.6 kPa, tensile strength (ISO 1798) of 125 kPa (min.) and an elongation at break (ISO 1798) of 210% (min.).

Cylindrical ring components having an inner diameter 3 mm and an outer diameter of 7.5 mm and a height 1.6 mm were cut from the foam material.

Test Method—Dose Consistency Upon Firing (without and with Delay)

1. Allow the filled aerosol container with its crimped valve (in the following pMDI unit") to stand at a temperature between 18° C. and 23° C. for at least 24 hours with the valve oriented upwards.
2. If applicable, place the pMDI unit to be tested into a plastic actuator to provide an inhaler (the release-to-fire, shuttle-type valves used in the following example need not be placed into an actuator, since the valve includes an integral nozzle) and subsequently prime the inhaler.
3. Collect the next three consecutive shots, in which for each individual shot the inhaler is shaken with a gentle rocking action through 180° inversion for at least 10 seconds and immediately fired (so that there is no delay between shaking and firing), into separate plastic USCA (Unit Sample Collection Apparatus) Medication Delivery collection tubes with filters ("USCA tubes"). The USCA apparatus is described in United States Pharmacopoeia vol. 29 (2006) section <601>. (These three shots will be referred to as shots numbers 1 to 3.)
3. Further collect the next three consecutive shots into separate USCA tubes, whereby for each individual shot the inhaler is shaken as described in step 3 and then fired after a time interval of 30 seconds upon cessation of shaking, so that there is a 30 seconds delay between shaking and firing. (These three shots will be referred to as shots numbers 4 to 6.)
4. Assay the dose of analyte collected in each USCA tube.

For testing release-to-fire type valves as used in the following example, the aforesaid method is slightly modified in that prior to shaking the inhaler, the valve stem is moved into its pre-firing (priming) position and held there during shaking and then released appropriately (i.e. either immediately or after 30 seconds delay in accordance with the described step) to cause valve firing.

It will be appreciated that a delay of 30 seconds as used in the aforesaid described method is particularly stringent.

The method of assaying the dose of drug analyte can be performed using any suitable analytical procedure known in the art. For examples herein using aerosol formulations containing suspended albuterol sulfate, the dose assay was conducted by collecting the dose of albuterol sulfate by washing the filter and tube with 25 ml of a diluent consisting of 0.1% phosphoric acid (55 parts), methanol (45 parts) and determining the amount of albuterol sulfate collected via High Performance Liquid Chromatography as well known in the art.

Figure 15A:
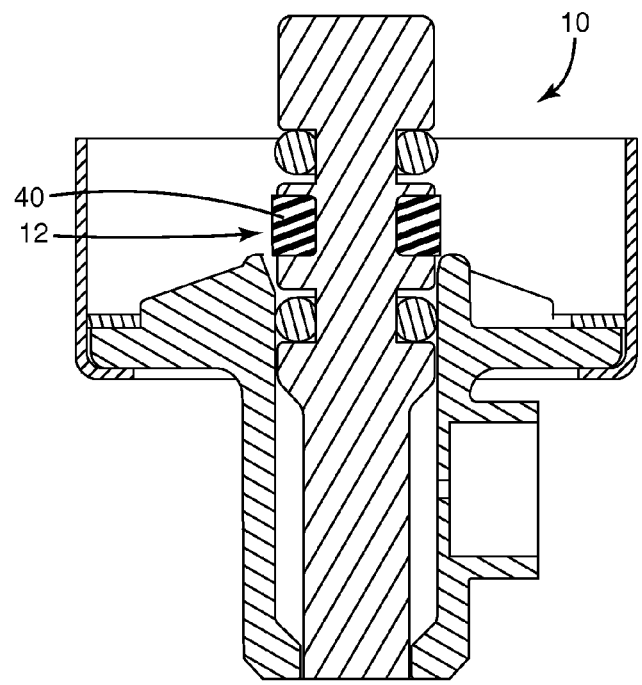
Figure 15B:
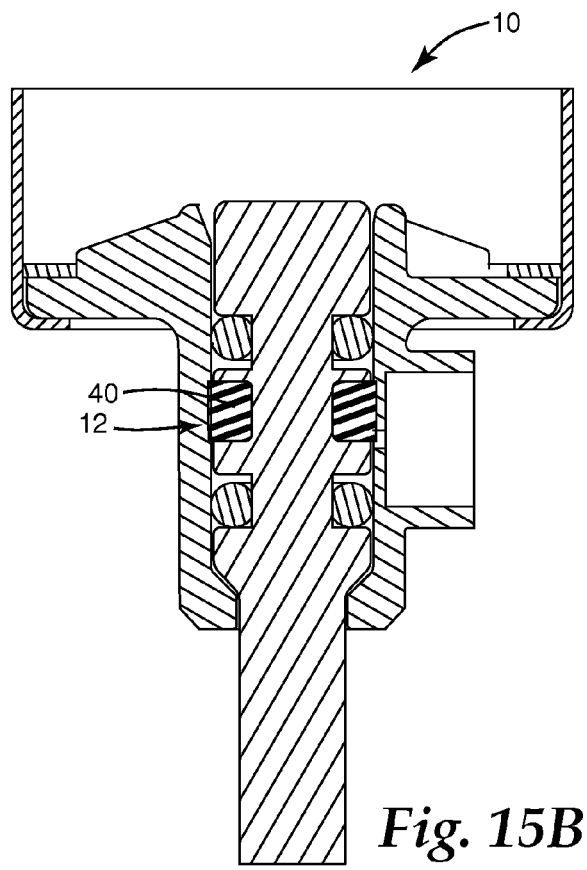
Figure 18:
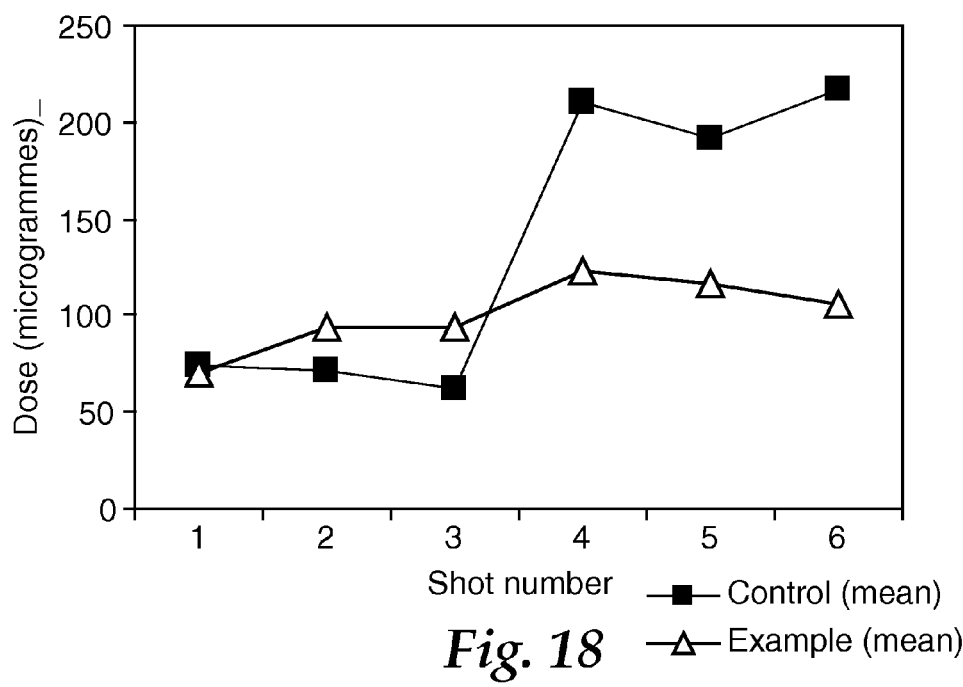
FIG. 18 illustrates results of dose consistency testing for exemplary inhalers.

Example and Controls 10 ml aluminum aerosol containers were cold filled with suspension formulation consisting of 1.97 mg/ml albuterol sulphate (having a majority of particles in the range 1 to 3 microns) and HFA 134a and then metering valves fitted with the aforesaid foam ring components in the metering chamber, e.g. generally similar to that shown in FIG. 15, (Examples) or without any ring components (Controls) were crimped onto the containers. The Examples and Controls were tested for dose consistency using the aforesaid method. The results (average of three replicates) are illustrated in FIG. 18. As can be appreciated from FIG. 18, the inhalers of the Example provided significantly more consistent dosing after a delay of 30 seconds in firing subsequent to shaking than did the Controls.

The invention claimed is:

1. A metered dose valve comprising an interior conduit, a metering chamber and at least one porous, fluid permeable, particulate semi-permeable body, said at least one porous body being positioned within a region of the interior conduit of the valve to hold medicament particles substantially uniformly dispersed within a volume of the porous body; wherein the porous body is permeable to at least particulates having a particle size of 250 microns or less and the porous body is impermeable to at least particulates having a particle size of 2 mm or more, and wherein the valve is a medicament-dispensing pressurized meter dose dispenser valve that dispenses a metered dose of an aerosol formulation comprising the medicament particles suspended in liquefied propellant.

2. A valve according to claim 1, wherein the at least one porous body is positioned within an internal chamber or within an internal channel within the valve leading to the metering chamber or within both said internal chamber and channel.

3. A valve according to claim 2, wherein the at least one porous body is positioned within an internal chamber, and wherein the internal chamber is the metering chamber or a pre-metering chamber.

4. A valve according to claim 1, wherein the valve comprises an internal channel leading into the metering chamber, wherein the at least one porous body is positioned within said internal channel.

5. A valve according to claim 4, wherein the valve comprises at least two porous bodies, wherein at least one porous body is positioned within said internal channel and at least one porous body is positioned within the metering chamber.

6. A valve according to claim 1, wherein the valve comprises a pre-metering chamber and the at least one porous body is positioned within the pre-metering chamber.

7. A valve according to claim 6, wherein the at least one porous body is positioned within the pre-metering chamber directly adjacent to the outlet(s) of the pre-metering chamber leading to the metering chamber—or the entrance(s) of a passageway from the pre-metering chamber to the metering chamber.

8. A valve according to claim 6, wherein the valve comprises an internal channel between the pre-metering chamber and the metering chamber and the at least one porous body is positioned within the pre-metering chamber and the internal channel.

9. A valve according to claim 8, wherein the valve comprises at least two porous bodies, wherein at least one porous body is positioned within the pre-metering chamber and at least one porous body is positioned within the internal channel.

10. A valve according to claim 6, wherein the valve comprises at least one additional porous body, said at least one additional porous body being positioned within the metering chamber.

11. A valve according to claim 1, wherein the porous body has a plurality of pores in particular 10 or more pores.

12. A valve according to claim-1, wherein the porous body has a relative density of 50% or less.

13. A valve according to claim 1, wherein the porous body comprises a material having a filamentous, fibrous and/or ligamentous structure.

14. A valve according to claim 1, wherein the porous body comprises a material having a relative density of 50% or less.

15. A valve according to claim 1, wherein the porous body comprises a material providing tortuous paths for passage of aerosol formulation.

16. A valve according to claim 1, wherein the porous body comprises a material selected from the group consisting of nonwovens, open-cell foams and reticulate open-cell foams.

17. A pressurized metered dose dispenser for dispensing a metered dose of an aerosol formulation comprising particles of a medicament suspended in liquefied propellant, optionally in combination with one or more excipients, the dispenser comprising an aerosol container equipped with a metered dose valve according to claim 1.

* * * * *

UNITED STATES PATENT AND TRADEMARK OFFICE
CERTIFICATE OF CORRECTION

PATENT NO.         : 9,067,031 B2                                              Page 1 of 2
APPLICATION NO.    : 12/444864
DATED              : June 30, 2015
INVENTOR(S)        : Jinks It is certified that error appears in the above-identified patent and that said Letters Patent is hereby corrected as shown below:

On the title page, item [56]

Page 2, Column 2 (Other Publications)
Line 6                          Delete "does" and insert -- dose --, therefor.

In the drawings

Sheet 19 of 19 (Y-axis) (Fig. 18)
Line 1                          Delete "(microgrammes)_" and insert -- micrograms) --, therefor.

In the specification

Figure 6:
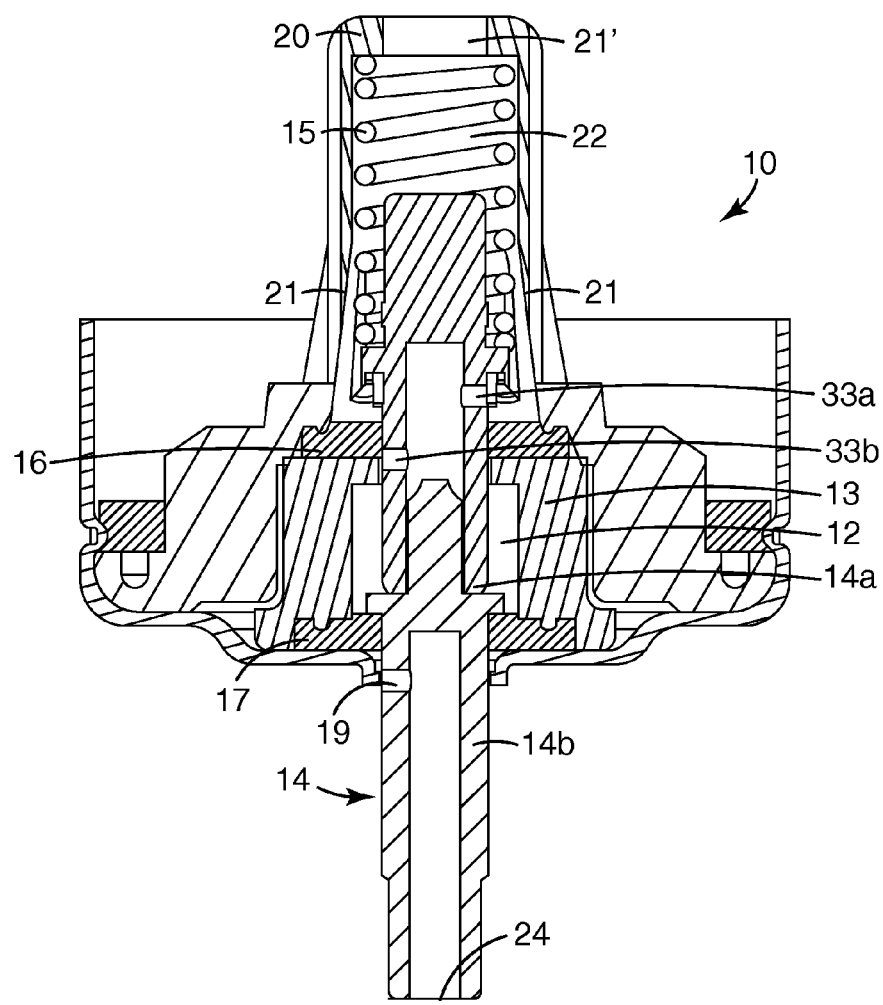
Figure 7:
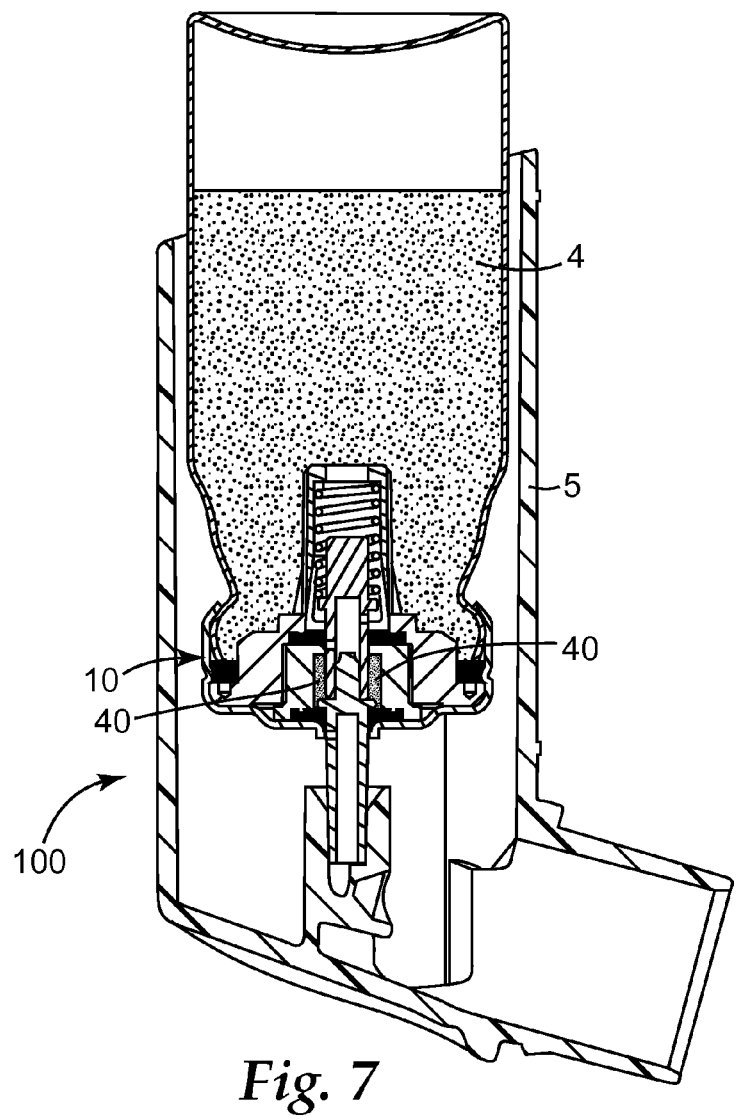
FIG. 7 represents a schematic cross-sectional view of an exemplary embodiment of a pressurized metered dose dispenser equipped with the valve shown in FIG. 6.

Column 4
Lines 27-29                     Delete "FIG. 7 represents ... valve shown in FIG. 6." and insert the
                                same on Col. 4, Line 26, as the continuation of the same paragraph.

Column 5
Line 10                         Delete "1 a," and insert -- 1a, --, therefor.
Line 11                         Delete "1 b," and insert -- 1b, --, therefor.
Line 29                         Delete "1 a," and insert -- 1a, --, therefor.
Line 48                         Delete "Morely" and insert -- Morley --, therefor.

Column 14
Line 52                         Delete "valve" and insert -- valve. --, therefor.

Column 18
Lines 16-17                     Delete "hypoglaecemics," and insert -- hypoglycemics, --, therefor.
Line 63                         Delete "benzodiazapines" and insert -- benzodiazepines --, therefor.
Line 64                         Delete "tomazeparm," and insert -- temazepam, --, therefor.

Signed and Sealed this
Seventeenth Day of May, 2016

Michelle K. Lee
*Director of the United States Patent and Trademark Office*

CERTIFICATE OF CORRECTION (continued)
U.S. Pat. No. 9,067,031 B2

In the specification

Column 19
| | |
|---|---|
| Line 13 | Delete "encamide" and insert -- encainide --, therefor. |
| Lines 22-23 | Delete "altoplase," and insert -- alteplase, --, therefor. |
| Line 24 | Delete "phenyloin, phenyloin" and insert -- phenytoin, phenytoin --, therefor. |
| Line 27 | Delete "mephenyloin," and insert -- mephenytoin, --, therefor. |
| Line 28 | Delete "secobarbitol" and insert -- secobarbital --, therefor. |
| Line 46 | Delete "trimprazine" and insert -- trimeprazine --, therefor. |
| Line 60 | Delete "keloconazole," and insert -- ketoconazole, --, therefor. |
| Line 62 | Delete "isoethionate," and insert -- isethionate, --, therefor. |
| Line 65 | Delete "cefutoxime axotil," and insert -- cefuroxime axetil, --, therefor. |

Column 20
| | |
|---|---|
| Line 17 | Delete "ethyltostosterone" and insert -- ethyltestosterone --, therefor. |
| Line 17 | Delete "enanihate," and insert -- enanthate, --, therefor. |
| Line 26 | Delete "calcitonion," and insert -- calcitonin, --, therefor. |
| Line 56 | Delete "Alakasurf" and insert -- Alaskasurf --, therefor. |

Column 21
| | |
|---|---|
| Line 23 | Delete "eucapyptus" and insert -- eucalyptus --, therefor. |
| Line 65 | Delete "proprionate," and insert -- propionate, --, therefor. |
| Line 66 | Delete "proprionate," and insert -- propionate, --, therefor. |

Column 22
| | |
|---|---|
| Lines 34-35 | Delete "proprionate)," and insert -- propionate), --, therefor. |

Column 23
| | |
|---|---|
| Line 38 | Delete "3. Further" and insert -- 4. Further --, therefor. |
| Line 44 | Delete "4. Assay" and insert -- 5. Assay --, therefor. |

In the claims

Column 24
| | |
|---|---|
| Line 51 | Claim 7, delete "chamber-or" and insert -- chamber or --, therefor. |

Column 25
| | |
|---|---|
| Line 3 | Claim 12, delete "claim-1," and insert -- claim 1, --, therefor. |